(12) United States Patent
Jain et al.

(10) Patent No.: US 12,178,799 B2
(45) Date of Patent: *Dec. 31, 2024

(54) TREATMENT FOR PRIMARY BILIARY CHOLANGITIS

(71) Applicant: Zydus Lifesciences Limited, Gujarat (IN)

(72) Inventors: Mukul R. Jain, Gujarat (IN); Deven V. Parmar, Gujarat (IN); Suresh Giri, Gujarat (IN); Binu Philip, Gujarat (IN); Pankaj Patel, Gujarat (IN)

(73) Assignee: Zydus Lifesciences Limited, Gujarat (IN)

( * ) Notice: Subject to any disclaimer, the term of this patent is extended or adjusted under 35 U.S.C. 154(b) by 103 days.

This patent is subject to a terminal disclaimer.

(21) Appl. No.: 17/880,949

(22) Filed: Aug. 4, 2022

(65) Prior Publication Data

US 2023/0201162 A1  Jun. 29, 2023

Related U.S. Application Data

(63) Continuation of application No. 17/512,950, filed on Oct. 28, 2021, now Pat. No. 11,433,050, which is a continuation of application No. 16/919,404, filed on Jul. 2, 2020, now abandoned, which is a continuation of application No. 15/835,938, filed on Dec. 8, 2017, now abandoned.

(30) Foreign Application Priority Data

Dec. 9, 2016 (IN) .............................. 201621042122

(51) Int. Cl.
| | |
|---|---|
| *A61K 31/40* | (2006.01) |
| *A61K 9/00* | (2006.01) |
| *A61K 31/575* | (2006.01) |
| *A61P 1/16* | (2006.01) |

(52) U.S. Cl.
CPC ............ *A61K 31/40* (2013.01); *A61K 9/0053* (2013.01); *A61K 31/575* (2013.01); *A61P 1/16* (2018.01)

(58) Field of Classification Search
CPC ..................................................... A61K 31/40
See application file for complete search history.

(56) References Cited

U.S. PATENT DOCUMENTS

| | | |
|---|---|---|
| 4,231,938 A | 11/1980 | Monaghan et al. |
| 4,346,227 A | 8/1982 | Terahara et al. |
| 4,444,784 A | 4/1984 | Hoffman et al. |
| 5,273,995 A | 12/1993 | Roth |
| 5,354,772 A | 10/1994 | Kathawala |
| 6,166,063 A | 12/2000 | Villhauer |
| 6,395,767 B2 | 5/2002 | Robl et al. |
| 6,699,871 B2 | 3/2004 | Edmondson et al. |
| 6,987,123 B2 | 1/2006 | Lohray et al. |
| 7,041,837 B2 | 5/2006 | Lohray et al. |
| 7,323,491 B2 | 1/2008 | Lohray et al. |
| 7,407,955 B2 | 8/2008 | Himmelsbach et al. |
| 8,110,598 B2 | 2/2012 | Lohray et al. |
| 8,212,057 B2 | 7/2012 | Lohray et al. |
| 8,558,009 B2 | 10/2013 | Lohray et al. |
| 8,772,342 B2 | 7/2014 | Darteil et al. |
| 9,610,277 B2 | 4/2017 | Patel et al. |
| 9,656,954 B2 | 5/2017 | Jain et al. |
| 9,783,495 B2 | 10/2017 | Pandey et al. |
| 9,814,697 B2 | 11/2017 | Patel et al. |
| 10,098,868 B2 | 10/2018 | Patel et al. |
| 10,385,017 B2 | 8/2019 | Desai et al. |
| 10,435,363 B2 | 10/2019 | Dwivedi et al. |
| 11,433,050 B2 * | 9/2022 | Jain .......................... A61P 1/16 |
| 11,872,209 B2 * | 1/2024 | Jain .......................... A61P 1/06 |

(Continued)

FOREIGN PATENT DOCUMENTS

| | | |
|---|---|---|
| DE | 102010012223 A1 | 9/2011 |
| EP | 1586571 A1 | 10/2005 |

(Continued)

OTHER PUBLICATIONS

US 11,147,794, 02/2003, Jain (withdrawn).*

(Continued)

*Primary Examiner* — Rei Tsang Shiao
(74) *Attorney, Agent, or Firm* — Goodwin Procter LLP

(57) ABSTRACT

The present invention provides therapeutic compound for prevention and treatment of primary biliary cholangitis, (PBC). Specifically, the present invention provides pharmaceutical composition comprising a compound of Formula (I) or a pharmaceutically acceptable salt thereof, for the treatment of PBC.

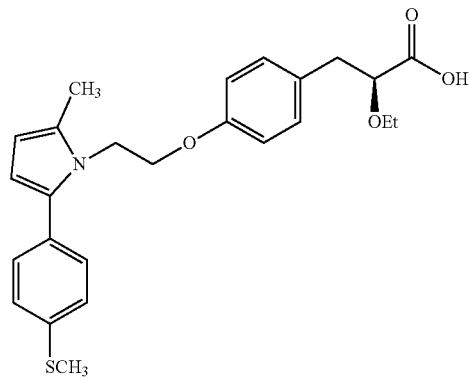

10 Claims, 1 Drawing Sheet

(56) References Cited

U.S. PATENT DOCUMENTS

| | | |
|---|---|---|
| 2003/0199498 A1 | 10/2003 | Lohray et al. |
| 2003/0236254 A1 | 12/2003 | Lohray et al. |
| 2007/0238776 A1 | 10/2007 | Lohray et al. |
| 2009/0196923 A1 | 8/2009 | Mandal et al. |
| 2011/0275669 A1 | 11/2011 | Lohray et al. |
| 2012/0121729 A1 | 5/2012 | Paterson et al. |
| 2013/0338209 A1 | 12/2013 | Gambhire et al. |
| 2015/0132289 A1 | 5/2015 | Ellis et al. |
| 2016/0068484 A1 | 3/2016 | Jain et al. |
| 2016/0107989 A1 | 4/2016 | Dwivedi et al. |
| 2016/0136131 A1 | 5/2016 | Patel et al. |
| 2016/0166539 A1 | 6/2016 | Patel et al. |
| 2016/0194280 A1 | 7/2016 | Dwivedi et al. |
| 2016/0207884 A1 | 7/2016 | Dwivedi et al. |
| 2017/0087127 A1 | 3/2017 | Patel et al. |
| 2017/0088514 A1 | 3/2017 | Gambhire et al. |
| 2017/0266158 A1 | 9/2017 | Patel et al. |
| 2017/0320823 A1 | 11/2017 | Jain et al. |
| 2018/0008616 A1 | 1/2018 | Pruzanski et al. |

FOREIGN PATENT DOCUMENTS

| | | |
|---|---|---|
| IN | 1910/MUM/2013 | 12/2014 |
| WO | WO-1991/019702 A1 | 12/1991 |
| WO | WO-1994/001420 A1 | 1/1994 |
| WO | WO-1994/013650 A1 | 6/1994 |
| WO | WO-1995/003038 A1 | 2/1995 |
| WO | WO-1995/017394 A1 | 6/1995 |
| WO | WO-1996/004260 A1 | 2/1996 |
| WO | WO-1996/004261 A1 | 2/1996 |
| WO | WO-1996/033998 A1 | 10/1996 |
| WO | WO-1997/025042 A1 | 7/1997 |
| WO | WO-1997/036579 A1 | 10/1997 |
| WO | WO-1999/008501 A2 | 2/1999 |
| WO | WO-1999/016758 A1 | 4/1999 |
| WO | WO-1999/019313 A1 | 4/1999 |
| WO | WO-1999/020614 A1 | 4/1999 |
| WO | WO-2000/023417 A1 | 4/2000 |
| WO | WO-2000/023445 A1 | 4/2000 |
| WO | WO-2000/023451 A1 | 4/2000 |
| WO | WO-2001/053257 A2 | 7/2001 |
| WO | WO-2002/024625 A2 | 3/2002 |
| WO | WO-2003/009841 A1 | 2/2003 |
| WO | WO-2005/031335 A1 | 4/2005 |
| WO | WO-2012/104869 A1 | 8/2012 |
| WO | WO-2012/145569 A1 | 10/2012 |
| WO | WO-2014/174524 A1 | 10/2014 |
| WO | WO-2014/195967 A2 | 12/2014 |
| WO | WO-2015/001573 A1 | 1/2015 |
| WO | WO-2015/011730 A1 | 1/2015 |
| WO | WO-2015/029066 A1 | 3/2015 |
| WO | WO-2015/033357 A2 | 3/2015 |
| WO | WO-2016/127019 A2 | 8/2016 |
| WO | WO-2016/181409 A1 | 11/2016 |
| WO | WO-2017/089979 A1 | 6/2017 |
| WO | WO-2017/089980 A1 | 6/2017 |

OTHER PUBLICATIONS

"Sodium Stearyl Fumarate", obtained on Jun. 23, 2015. Retrieved from the Internet: <URL: https://www.medicinescomplete.com/me/excipients/current/ . . . >, 4 pages.

Acdisol Product Overview (year 2005).

Angulo et al. (2000) "Oral Budesonide in the Treatment of Patients with Primary Biliary Cirrhosis With a Suboptimal Response to Ursodeoxycholic Acid," *Hepatology* 31(2):318-323.

Angulo, P. (2007) "GI Epidemiology: nonalcoholic fatty liver disease," *Aliment. Pharmacol. Ther.* 25(8)883-889.

Anonymous "IND Minutes draft 19 07 12" Retrieved on Oct. 15, 2013 from the Internet from URL: http://www.docstoc.com/docs/145152750/IND-Minutes-draft-19-07-12 (1 page).

Anonymous "Lipaglyn™ Discovery, Development & Preclinical Studies" Retrieved on Oct. 15, 2013 from the Internet from URL: http://webcache.googleusercontent.com/search?q=cache:RGrhmY0HM3sJ:lipaglyn.com/downloads/Lipaglyn_Preclinical_Studies.ppsx (25 pages).

Anonymous International Nonproprietary Names for Pharmaceutical Substances (INN); Jan. 1, 2012; Retrieved from the internet: URL: http://www.who.int/medicines/publications/druginformation/issues/PL_108.pdf; Retrieved on Oct. 15, 2013; pp. 401-471.

Ansel et al. (1999) "Pharmaceutical Dosage Forms and Drug Delivery Systems, Seventh Edition" 88-92.

Arnett, E. M. et al. (1965) "Solvent Effects in Organic Chemistry. V. Molecules, Ions, and Transition States in Aqueous Ethanol," *J. Am. Chem. Soc.* 87(7)1541-1553.

Augustyns, K et al. (2005) "Inhibitors of proline-specific dipeptidyl peptidases: DPP IV inhibitors as a novel approach for the treatment of Type 2 diabetes," *Expert Opin. Ther. Patents* 15(10)1387-1407.

Barb et al. (2016) "Pharmacological management of nonalcoholic fatty liver disease" Metabolism Clinical and Experimental 65:1183-1195.

Berge, S. M. et al. (1977) "Pharmaceutical Salts," *J. Pharmaceutical Sciences* 66(1):1-19.

Berger et al. (2005) "PPARs: Therapeutic targets for metabolic disease" TRENDS in Pharmacological Sciences 26(5): 244-251.

Beuers et al.(2015) "New paradigms in the treatment of hepatic cholestasis: From UDCA to FXR, PXR and beyond," *Journal of Hepatology*, 62(1): S25-S37.

Bharate, S. et al. (2010) "Interactions and incompatibilities of pharmaceutical excipients with active pharmaceutical ingredients: a comprehensive review." *J. Excipient and Food Chem.* 1(3)3-26.

Boettcher, E. et al. (2012) "Meta-analysis: pioglitazone improves liver histology and fibrosis in patients with non-alcoholic steatohepatitis," *Aliment. Pharmacol. Ther.* 35(1)66-75. (Abstract Only, Retrieved from https://www.ncbi.nih.gov/pubmed/22050199).

Boulet, L-P. (2009) "Influence of Comorbid Conditions on Asthma" *European Respiratory Journal* 33:897-906.

Brenna, E. et al. (2009) "Enzyme-mediated synthesis of EEHP and EMHP, useful pharmaceutical intermediates of PPAR agonists" *Tetrahedron: Asymmetry* 20:2594-2599.

Bugianesi, E. et al. (2005) "Insulin Resistance: A Metabolic Pathway to Chronic Liver Disease," *Hepatology* 42(5):987-1000.

Cairns, D. (editor) "Essentials of Pharmaceutical Chemistry, Fourth Edition" 2012, p. 14.

Chatila, W. M. et al. "Comorbidities in Chronic Obstructive Pulmonary Disease" *Proc. Am. Thorac. Soc.* (2008) vol. 5, pp. 549-555.

Chaumeil, J. C. "Micronization: A Method of Improving the Bioavailability of Poorly Soluble Drugs," *Meth. Find. Exp. Clin. Pharmacol.* (1998) vol. 20, No. 3, pp. 211-215.

Cheung et al. (2015) "Time to make the change from 'primary biliary cirrhosis' to 'primary biliary cholangitis'," *Can J Gastroenterol Hepatol*, 29:293.

Choi, W. S. et al. (2004) "Amorphous ultrafine particle preparation for improvement of bioavailability of insoluble drugs: grinding characteristics of fine grinding mills," *Int. J. Miner. Process.* 74S:S165-S172.

Chou et al. (2013) "Metrelepin: First Global Approval" Drugs 73:989-997.

Cuperus et al. (2014) "Fibrate treatment for primary biliary cirrhosis," *Curr Opin Gastroenterol* 30(3):279-286.

Deeg et al. (2007) "Pioglitazone and Rosiglitazone Have Different Effects on Serum Lipoprotein Particle Concentrations and Sizes in Patients With Type 2 Diabetes and Dyslipidemia" Diabetes Care 30(10):2458-2464.

Demuth, H.-U. et al. (2005) "Type 2 diabetes—Therapy with dipeptidyl peptidase IV inhibitors," *Biochim. Biophys. Acta*, 1751:33-44.

Duval et al (2002) "The role of PPARs in atherosclerosis," *TRENDS in Molecular Medicine* 8(9):422.

Fan, W. and Evans, R. (2015) "PPARs and ERRs: molecular mediators of mitochondrial metabolism" *Curr. Opin. Cell Bio.* 33:49-54.

FDA approves Ocaliva for rare, chronic liver disease, FDA Press Release, May 31, 2016, retrieved from: https://www.fda.gov/news-events/press-announcements/fda-approves-ocaliva-rare-chronic-liver-disease.

(56) References Cited

OTHER PUBLICATIONS

FDA News Release—FDA Approves Egrifta to treat Lipodystrophy in HIV Patients; downloaded from www.fda.gov/NewsEvents/Newsroom/PressAnnouncements/ucm233516.htm on Sep. 7, 2016 (2 pages).
Gennaro et al. "Remington's Pharmaceutical Sciences, 19th Edition" (1995) Mack Publishing, pp. 1380-1383.
Ghonem et al., "Fibrates and Cholestasis," *Hepatology*, 62:635-643 (2015).
Giri et al. "Efficacy of Saroglitazar, a Novel PPAR Agonist in a Mouse Model of Non-Alcoholic Steatohepatitis" Poster No. 2011, Keystone Symposia Conference, Mar. 22-27, 2015 at Whistler, British Colombia, Canada.
Hadigan, C. et al. (2004) "Metabolic Effects of Rosiglitazone in HIV Lipodystrophy: A Randomized, Controlled Trial," *Ann. Internal Med.* 140(10):788-794. (Abstract Only).
Herrine, S. K. "Nonalcoholic Steatohepatitis (NASH)" *Merck Manual* (Revised May 2016) Retrieved on Sep. 13, 2017 from http://www.merckmanuals.com/professional/hepatic-and-biliary-disorders/approach-to-the-patient-with-liver-disease/nonalcoholic-steatohepatitis-nash. (3 pages).
Hirschfield et al. (2015) "Efficacy of Obeticholic Acid in Patients With Primary Biliary Cirrhosis and Inadequate Response to Ursodeoxycholic Acid," *Gastroenterology* 148(4):751-761.
Honda et al. (2013) "Anticholestatic effects of Bezafibrate in Patients with Primary Biliary Cirrhosis Treated With Ursodeoxycholic Acid," Hepatology, 57:1931-1941.
Hosonuma et al. (2015) "A Prospective Randomized Controlled Study of Long-Term Combination Therapy Using Ursodeoxycholic Acid and Bezafibrate in Patients With Primary Biliary Cirrhosis and Dyslipidemia," *Am J Gastroenterol* 110:423-431.
Ikegami et al. (2008) "Ursodeoxycholic acid: Mechanism of action and novel clinical applications," *Hepatology Research* 38:123-131.
IND Committee: "Minutes of IND Committee Meeting Held on Jul. 19, 2012" Retrieved on Oct. 15, 2013 from the Internet from URL: http://www.docstoc.com/docs/145152750/IND-Minutes-draft-19-07-12. (2 pages).
International Preliminary Report on Patentability dated Aug. 15, 2013 for International Application No. PCT/IN2012/000069 (5 pages).
International Preliminary Report on Patentability dated Dec. 1, 2015 for International Patent Application No. PCT/IN2014/000367 (9 pages).
International Preliminary Report on Patentability dated Jul. 9, 2015 for International Application No. PCT/IN2013/000391 (9 pages).
International Preliminary Report on Patentability dated Mar. 1, 2016 for Application No. PCT/IN2014/000551 (7 pages).
International Preliminary Report on Patentability dated Mar. 8, 2016 for International Patent Application No. PCT/IN2014/000584 (10 pages).
International Preliminary Report on Patentability dated Oct. 6, 2015 for International Patent Application No. PCT/IN2014/000445 (7 pages).
International Preliminary Report on Patentability mailed on Oct. 9, 2015 for International Application No. PCT/IN2014/000489 (7 pages).
International Search Report and Written Opinion dated Dec. 19, 2014 for Application No. PCT/IN2014/000551 (11 pages).
International Search Report and Written Opinion dated Dec. 23, 2014 for International Patent Application No. PCT/IN2014/000445 (10 pages).
International Search Report and Written Opinion dated Feb. 2, 2015 for International Patent Application No. PCT/IN2014/000367 (14 pages).
International Search Report and Written Opinion dated Mar. 23, 2015 for Application No. PCT/IN2014/000584 (14 pages).
International Search Report and Written Opinion dated Nov. 20, 2013 for International Application No. PCT/IN2013/000391 (13 pages).
International Search Report and Written Opinion mailed on Nov. 20, 2014 for International Application No. PCT/IN2014/000489 (10 pages).
International Search Report dated May 9, 2012 for International Application No. PCT/IN2012/000069 (3 pages).
Jackson, K. "No Benefit from Ezetimibe in NASH" In Medpage Today (Jun. 2015).
Jain et al (2015) "Saroglitazar, a novel PPARα/γ agonist with predominant PPARα activity, shows lipid-lowering and insulin-sensitizing effects in preclinical models," *Pharmacol Res Perspect.*; 3(3):e00136.
Jain et al.(2018) "Dual PPARα/γ agonist saroglitazar improves liver histopathology and biochemistry in experimental NASH models," *Liver Int.* 38(6):1084-1094.
Jain et al. "Saroglitazar Shows Therapeutic Benefits in Mouse Model of Non-alcoholic Fatty Liver Disease (NAFLD) and Non-alcoholic Steatohepatitis (NASH)" Poster No. 1957-P, 75th Scientific Session—ADA, Jun. 5-9, 2015, Boston, MA, USA.
Jain et al. (2017) "Saroglitazar, a novel first in class drug discovered & developed in India for management of diabetic dyslipidemia and related metabolic conditions," "Pharmacologists of India Their Contribution" published by Vallabh Prakashan: book chapter 30, p. 246-261.
Jani, R. H. et al. (2013) "Pharmacokinetics, Safety, and Tolerability of Saroglitazar (ZYH1), a Predominantly PPARα Agonist with Moderate PPARγ Agonist Activity in Healthy Human Subjects" *Clin. Drug Investig.* 33:809-816.
Jani, R. H. et al. (2009) "A Prospective Randomized, Double Blind, Placebo Controlled Study to Evaluate the Safety, Tolerability and Pharmacokinetics of ZYH1 Following Once a Day (OD) Oral Administrations up to 10 Days in Healthy Volunteers," *Diabetes* (2009) 58(No. Suppl. 1):A569.
Jani, R. H. et al. (2014) "A Multicenter, Prospective, Randomized, Double-Blind Study to Evaluate the Safety and Efficacy of Saroglitazar 2 and 4 mg Compared with Placebo in Type 2 Diabetes Mellitus Patients Having Hypertriglyceridemia Not Controlled with Atorvastatin Therapy (Press VI)," *Diabetes Technology & Therapeutics*, 16(2):63-71.
Kandel et al.(2016) "Genomewide comparison of the inducible transcriptomes of nuclear receptors CAR, PXR and PPARα in primary human hepatocytes," *Biochimica et Biophysica Acta (BBA)—Gene Regulatory Mechanisms*, 1859(9):1218-1227.
Kaplan et al. (2005) "Primary Biliary Cirrhosis," *N Engl J Med* 353:1261-1273.
Kurihara et al. (2000) Effect of Bezafibrate in the Treatment of Primary Biliary Cirrhosis, *Current Therapeutic Research*, 61(2):74-82.
LaBrecque, D. et al. (2012) "World Gastroenterology Organisation, Global Guidelines: Nonalcoholic Fatty Liver disease and Nonalcoholic Steatohepatitis (long version)" World Gastroenterology Organisation 29 pages.
Lemoine, M. et al. "Steatohepatitis (fatty liver) Is Associated With Increased Hepatic Expression of SREBP-1 In HIV-Infected Patients With Antiretroviral Therapy-Linked Lipodystrophy," Abstract from 55th Annual Meeting of the American Association for the Study of Liver Diseases, Oct. 29 to Nov. 2, 2004; Printed from http://www.natap.org/2004/AASLD/aasld_10.htm. (8 pages).
Leuschner et al. (1999) "Oral Budesonide and Ursodeoxycholic Acid for Treatment of Primary Biliary Cirrhosis: Results of a Prospective Double-Blind Trial," *Gastroenterology* 117:918-925.
Lieberman, et al. (1989) "Pharmaceutical Dosage Forms: Tablets, vol. 1, 2nd Edition" Marcel Dekker Inc., pp. 111-114.
Macallan, D. C. et al. (2008) "Treatment of Altered Body Composition in HIV Associated Lipodystrophy: Comparison of Rosiglitazone, Pravastatin, and Recombinant Human Growth Hormone," *HIV Clinical Trials*, 9(Issue 4):254-268. (Abstract Only).
Package Insert for ACTOS (pioglitazone) tablets for oral use (2013).
Package Insert for AVANDIA (rosiglitazone maleate) Tablets (2008).
Pai, V. et al. (2014) "A Multicenter, Prospective, Randomized, Double-blind Study to Evaluate the Safety and Efficacy of Saroglitazar 2 and 4 mg Compared to Pioglitazone 45 mg in Diabetic Dyslipidemia (Press V)." *J. Diabetes Sci. Technol.* 8(1):132-141.

(56) References Cited

OTHER PUBLICATIONS

Palomer et al. (2016) "PPARβ/δ and lipid metabolism in the heart" Biochemica et Biophysica Acta 1861:1569-1578.
Pharmatrans Sanaq AG "LubriSanaq" Dated Feb. 5, 2008. (2 pages).
Pivovarova et al (2011) "All signs of the metabolic syndrome in hypertensive ISIAH rats are associated with increased activity of the transcription factors PPAR, LXR, PXR, and CAR in the liver," *Biochem. Moscow Suppl. Ser. B* (5):29-36.
Poupon (2003) "Autoimmune overlapping syndromes," *Clin Liver Dis* 7:865-878.
Prescribing Information for Zetia® (ezetimibe; year 2012).
Pubchem CID 31401 Ursodiol [online Retrieved from the internet, [Retrieved on Oct. 26, 2018], <url: https://pubchem.ncbi.nlm.nih.gov/compound/ursodeoxycholic_acid#section=Top> (Year: 2006).
Pubchem CID 60151560 Saroglitazar [online] Retrieved from the internet, [Retrieved on Oct. 26, 2018], <url: https://pubchem.ncbi.nlm.nih.gov/compound/60151560> (Year: 2012).
Rabahi et al. (2010) "Triple therapy with ursodeoxycholic acid, budesonide and mycophenolate mofetil in patients with features of severe primary biliary cirrhosis not responding to ursodeoxycholic acid alone," *Gastroenterol Clin. Biol.* 34:283-287.
Rakoski, M. et al. (2010) "Meta-analysis: Insulin Sensitizers for the Treatment of Non-alcoholic Steatohepatitis" *Aliment. Pharmacol. Ther.* 32:1211-1221.
Ramirez, T. et al. (2012) "Structural Correlates of PPAR Agonist Rescue of Experimental Chronic Alcohol-Induced Steatohepatitis," *J. Clin. Exper. Pathology* 2(4):1-9.
Response to Written Opinion filed on May 21, 2015 for International Application No. PCT/IN2014/000489 (6 pages).

Seo, Y. S. et al. (2008) "PPAR agonists treatment is effective in a nonalcoholic fatty liver disease animal model by modulating fatty-acid metabolic enzymes" *J. Gatroenterology Hepatology* (2008) 23(1)102-109.
Sui et al.(2010) "Deficiency of PXR decreases atherosclerosis in apoE deficient mice," *J. Lipid Res.* 51:1652-1659.
Talwalkar et al. (2005) "Mycophenolate Mofetil for the Treatment of Primary Biliary Cirrhosis in Patients With an Incomplete Response to Ursodeoxycholic Acid," *J Clin Gastroenterol* 39(2):168-171.
Tungsiripat, M. et al. (2010) "Rosiglitazone improves lipoatrophy in patients receiving thymidine-sparing regimens," *AIDS* 24:1291-1298.
USPTO Trademark Database Entry for AEROSIL.
Van Wijk, J. P. H. et al. (2005) "Comparison of Rosiglitazone and Metformin for Treating HIV Lipodystrophy: A Randomized Trial," *Ann. Internal Med.* 143(5)337-346.
Vleggaar et al. (2001) "Jaundice in non-cirrhotic primary biliary cirrhosis: the premature ductopenic variant," *Gut* 49:276-281.
Wallace et al. (2010) "The PXR is a drug target for chronic inflammatory liver disease," *Journal of Steroid Biochemistry & Molecular Biology* 120:137-148.
Written Opinion of the International Searching Authority dated May 9, 2012 for International Application No. PCT/IN2012/000069 (4 pages).
Yessoufou et al. (2010) "Multifaceted roles of peroxisome proliferator-activated receptors (PPARs) at the cellular and whole organism levels" Swiss Medical Weekly 140:w13071.
Yin et al. (2015) "Systematic review and meta-analysis: bezafibrate in patients with primary biliary cirrhosis," *Drug Design, Development and Therapy* 9:5407-5419.

\* cited by examiner

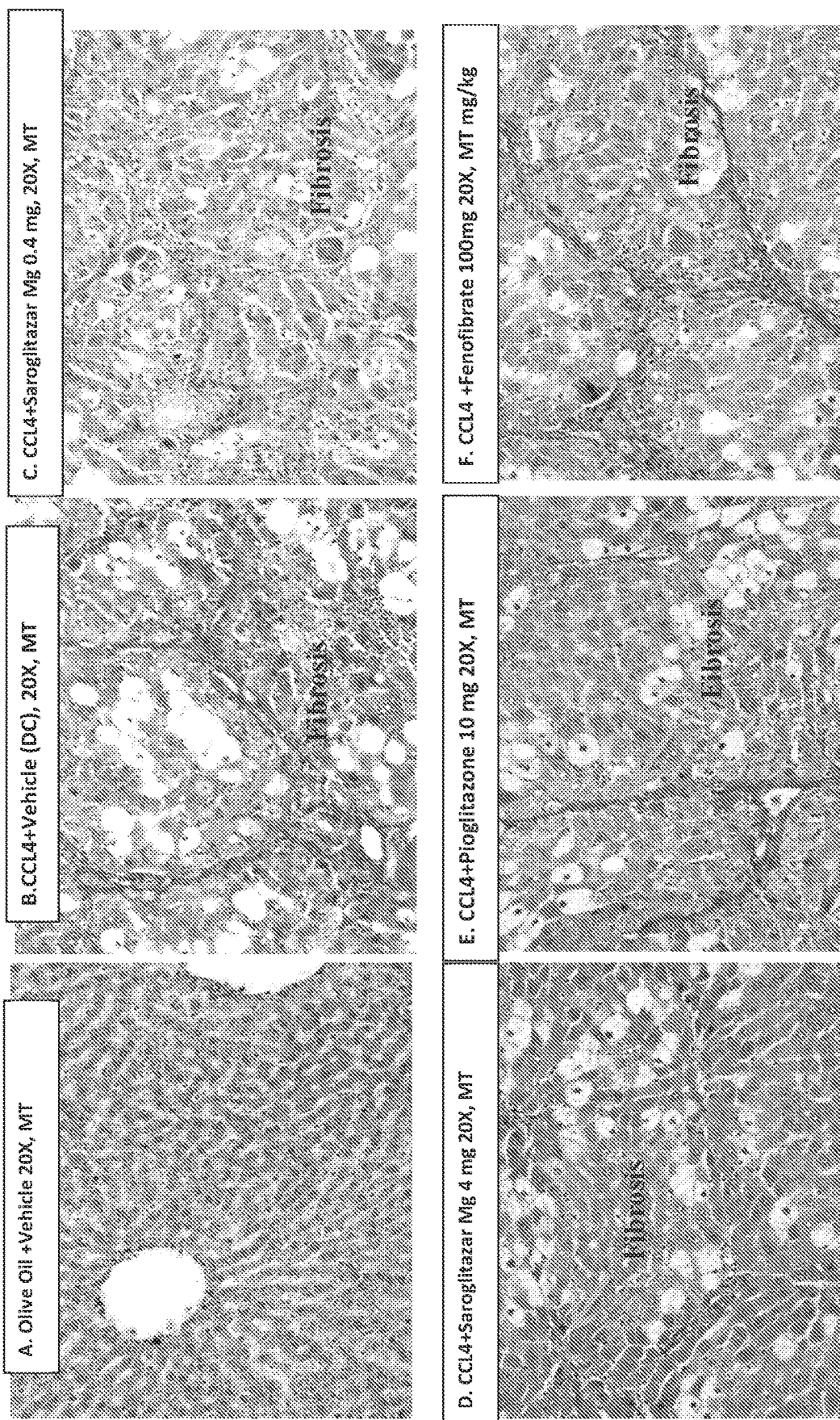

TREATMENT FOR PRIMARY BILIARY CHOLANGITIS

RELATED APPLICATIONS

This application is a continuation patent application under 35 U.S.C. § 120 of U.S. patent application Ser. No. 17/512,950, filed on Oct. 28, 2021, which application is a continuation patent application of U.S. patent application Ser. No. 16/919,404, filed on Jul. 2, 2020, which application is a continuation patent application of U.S. patent application Ser. No. 15/835,938, filed on Dec. 8, 2017, which application claims the benefit of and priority to Indian Patent Application No. 201621042122, filed Dec. 9, 2016; the contents of which are hereby incorporated by reference in their entirety.

FIELD OF THE INVENTION

The present invention is related to the development of therapeutic compound for prevention and treatment of primary biliary cholangitis, (PBC). Specifically, the present invention provides the use of Saroglitazar and its pharmaceutically acceptable salts for the treatment of PBC.

BACKGROUND OF THE INVENTION

Primary biliary cholangitis, (PBC) is a chronic inflammatory autoimmune disease that mainly targets the cholangiocytes of the interlobular bile ducts in the liver. The condition primarily affects middle-aged women. Without treatment, PBC generally progresses to cirrhosis and eventually liver failure over a period of 10-20 years. PBC is a rare disease with prevalence of less than 1/2000. PBC is thought to result from a combination of multiple genetic factors and superimposed environmental triggers. The contribution of the genetic predisposition is evidenced by the familial clustering. Several risk factors, including exposure to infectious agents and chemical xenobiotics, have been suggested. The detection of serum antimitochondrial antibodies (AMA) and increased levels of immunoglobulin M (IgM) are biochemical features of this disease along with biochemical evidence of cholestasis with elevation of alkaline phosphatase activity. Histopathologically, it is characterized by portal inflammation and the slow progressive destruction of the portal interlobular bile ducts due to chronic non-suppurative cholangitis. The loss of bile ducts leads to cholestasis, which leads to further hepatic damage, fibrosis, cirrhosis, and ultimately, liver failure (Kaplan M M, Gershwin M E. Primary biliary cirrhosis. N Engl J Med, 353, 2005, 1261-1273). There are three major forms of PBC. The typical or classical form is represented by the slowly progressive decline of small bile ducts and parallel increase in liver fibrosis, leading to biliary cirrhosis over a period of 10-20 years. A second form, which affects 10-20% of patients, is characterised by the fluctuating or persistent presence of the features of Autoimmune hepatitis (AIH) (R. Poupon Autoimmune overlapping syndromes, Clin Liver Dis, 7, 2003, pp. 865-878). These patients have a more severe disease course, with early development of liver fibrosis and liver failure. A third form, which affects 5-10% of patients, is represented by the so-called premature ductopenic variant (F. P. Vleggaar, H. R. van Buuren, P. E. Zondervan, F. J. ten Kate, W. C. Hop, Jaundice in non-cirrhotic primary biliary cirrhosis: the premature ductopenic variant, Gut, 49, 2001, 276-281). Its hallmark is a very rapid onset of ductopenia and severe icteric cholestasis, progressing very quickly towards cirrhosis in less than 5 years.

Ursodeoxycholic acid (UDCA) [(Ikegami T, Matsuzaki Y. Ursodeoxycholic acid: mechanism of action and novel clinical applications. Hepatol Res, 38, 2008, 123-131] and Obeticholic acid [FDA approves Ocaliva for rare, chronic liver disease, FDA Press Release, May 31, 2016] are currently the only FDA-approved medical treatment for PBC. When administered at doses of 13-15 mg/kg/day, a majority of patients with PBC have a normal life expectancy without additional therapeutic measures. One out of three patients does not adequately respond to UDCA therapy and may need additional medical therapy and/or liver transplantation. Certain fibrates such as Bezafibrates have been tried on patients that does not respond sufficiently to ursodeoxycholic acid (UDCA) monotherapy (Honda, A., Ikegami, T., Nakamuta, M., Miyazaki, T., Iwamoto, J., Hirayama, T., Saito, Y., Takikawa, H., Imawari, M. and Matsuzaki, Y. Anticholestatic effects of bezafibrate in patients with primary biliary cirrhosis treated with ursodeoxycholic acid. Hepatology, 57, 2013, 1931-1941), but with limited success. Immunosuppressive medication is not recommended as the first-line, alternative drug for PBC, but budesonide, a non-halogenated glucocorticoid with a high first-pass metabolism, and/or mycophenolate mofetil, an inhibitor of the purine biosynthetic pathway which is critical to lymphocytic proliferation and activation, are sometimes used in patients who fail to respond to UDCA (Leuschner M, Maier K P, Schlichting J, Strahl S, Herrmann G, Dahm H H, et al. Oral budesonide and ursodeoxycholic acid for treatment of primary biliary cirrhosis: results of a prospective double-blind trial. Gastroenterology 1999; 117: 918-925; Rabahi N, Chretien Y, Gaouar F, Wendum D, Serfaty L, Chazouilleres O, et al. Triple therapy with ursodeoxycholic acid, budesonide and mycophenolate mofetil in patients with features of severe primary biliary cirrhosis not responding to ursodeoxycholic acid alone. Gastroenterol Clin. Biol. 34, 2010, 283-287). However, the effects of these immunosuppressive agents remain controversial (Angulo P, Jorgensen R A, Keach J C, Dickson E R, Smith C, Lindor K D, Oral budesonide in the treatment of patients with primary biliary cirrhosis with a suboptimal response to ursodeoxycholic acid, Hepatology, 31, 2000, 318-323; Talwalkar J A, Angulo P, Keach J C, Petz J L, Jorgensen R A, Lindor K D. Mycophenolate mofetil for the treatment of primary biliary cirrhosis in patients with an incomplete response to ursodeoxycholic acid, J Clin Gastroenterol 39, 2005, 168-171). Several other therapies have been tried for e.g. DE102010012223, US2015132289, WO2016127019, WO2012145569 to cite a few. However, looking at the substantial unmet need there exists a need for newer therapies for the treatment of PBC.

WO 03009841 discloses compounds of the following general formula (A)

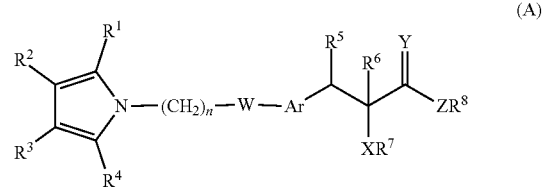

These compounds are reported to be hypolipidaemic agents. This document also discloses sodium and calcium salts of some of the compounds disclosed therein.

WO 2012/104869 discloses Saroglitazar (I) and its Magnesium salt being effective in the treatment of lipohypertrophy, lipoatrophy and metabolic abnormalities in HIV patients.

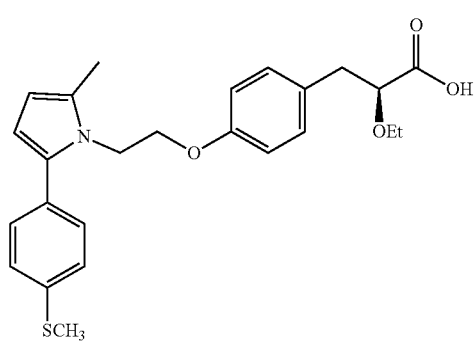
(I)

WO 2014/174524 discloses the use of Saroglitazar (I) and its pharmaceutically acceptable salts for the treatment of Non-alcoholic Fatty Liver Diseases (NAFLD) & Nonalcoholic Steatohepatitis (NASH). Indian provisional application 1850/MUM/2015 discloses the use of Saroglitazar and its pharmaceutically acceptable salts for the treatment of chylomicronemia. Indian provisional application 4430/MUM/2015 discloses the use of the compound (I) and its pharmaceutically acceptable salts for the treatment of nephropathy. Indian provisional application 4431/MUM/2015 discloses the use of the compound (I) and its pharmaceutically acceptable salts for the treatment of retinopathy. Disclosed herein are the use of the compound (I) and its pharmaceutically acceptable salts for the treatment of primary biliary cholangitis.

OBJECTIVE OF THE INVENTION

In one embodiment, the present invention discloses a pharmaceutical composition containing the compound of the formula (I) or its pharmaceutically acceptable salts for treatment of primary biliary cholangitis (PBC) in patient in need of such treatment.

In another embodiment the present invention provides a method and a formulation comprising an effective amount of compound of Formula (I) or its pharmaceutically acceptable salts for treating primary biliary cholangitis (PBC). The method comprises administering to a subject an effective amount of a compound of formula (I), as a pharmaceutical formulation, as disclosed hereinafter including pharmaceutically acceptable salts of the compound of formula (I).

In yet another embodiments the invention further provides a pharmaceutical composition containing effective amount of compound of formula (I) or its pharmaceutically acceptable salts suitable for treatment of primary biliary cholangitis (PBC).

In another embodiment the present invention provides a method of treating primary biliary cholangitis (PBC) in a subject, comprising administering to the subject an effective amount of a compound according to Formula (I), or a pharmaceutically acceptable salts thereof as a suitable pharmaceutically acceptable composition.

In a further embodiment is provided use of compound of formula (I) or its pharmaceutically acceptable salts for the treatment of primary biliary cholangitis (PBC).

The above and other embodiments of the present invention are disclosed further hereinafter.

BRIEF DESCRIPTIONS OF DRAWINGS

FIG. 1. Effect on liver histology using Masson's trichrome staining (20×) in two weeks $CCl_4$ administered SD rats treated with Saroglitazar Magnesium along with $CCl_4$ administration for 4 weeks.

DETAILED DESCRIPTION OF THE INVENTION

The present invention describes a pharmaceutical composition for reduction and removal of lipid accumulated in the liver cells (hepatocytes), required for treating and preventing certain diseases and conditions in a subject suffering primary biliary cholangitis (PBC) and methods for ameliorating and/or treating such disease conditions. Also provided are compounds for reduction and removal of lipid accumulated in the liver cells (hepatocytes), required for treating and preventing certain diseases and conditions in a subject suffering primary biliary cholangitis (PBC) and methods for ameliorating and/or treating such disease conditions In certain aspects, the formulation comprises compound of formula (I) or its pharmaceutically acceptable salts, and the method comprises administering to a subject in need thereof an effective amount of the compound according to Formula (I), or a pharmaceutically acceptable salt thereof.

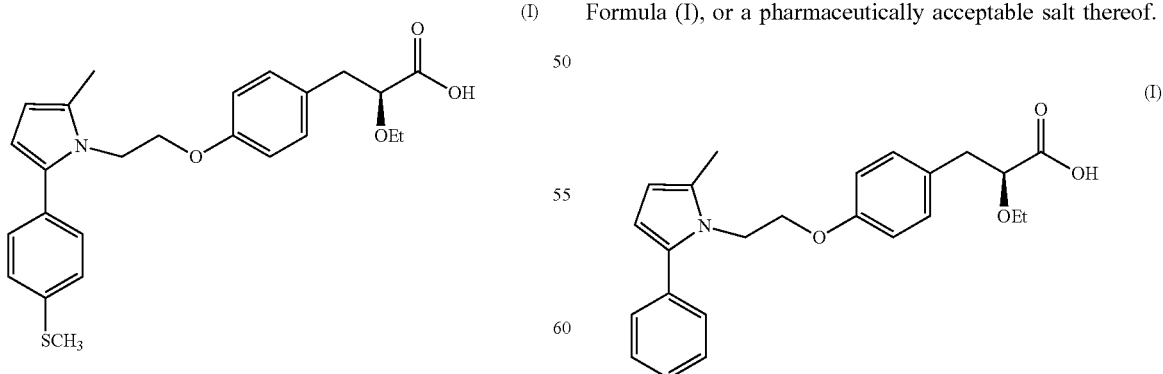
(I)

In a preferred embodiment the pharmaceutically acceptable salts are selected from metal cations. In a further preferred embodiment, the pharmaceutically acceptable salts are selected from Na+, K+, Ca+2, Mg+2 and the like. In a particularly preferred embodiment, the compound is the Magnesium salt having formula 1(a)

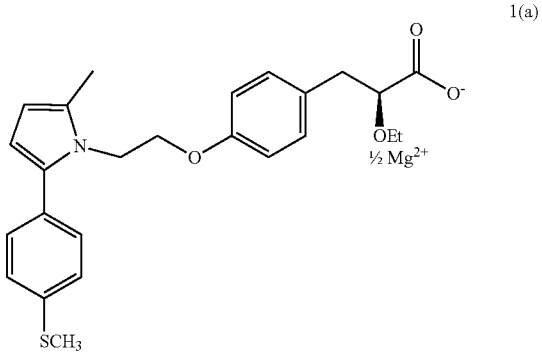

Definitions and Abbreviations

As used above, and throughout this disclosure, the following terms, unless otherwise indicated, shall be understood to have the following meanings;

"Patient" includes both human and animals. "Mammal" means humans and other mammalian animals.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

As used herein "treating" includes achieving, partially or substantially, one or more of the following results: partially or totally reducing the extent of the disease, disorder or syndrome (e.g., reducing fat deposits, increasing insulin activity/sensitivity, reducing weight); ameliorating or improving a clinical symptom or indicator associated with the disorder; delaying, inhibiting or preventing the progression of the disease, disorder or syndrome; or partially or totally delaying, inhibiting or preventing the onset or development of disorder. Delaying, inhibiting or preventing the progression of the disease, disorder or syndrome includes for example, delaying, inhibiting or preventing the progression of PBC; and delaying, inhibiting or preventing the progression of pre-diabetes to diabetes.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates.

One or more compounds of the invention may optionally be converted to a solvate. Preparation of solvates is generally known. Thus, for example, M. Caira et al, J. Pharmaceutical Sci, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, AAPS Pharm Sci Tech., 5(1), article 12 (2004); and A. L. Bingham et al, Chem. Commun., 603-604 (2001)

The compounds of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contain both a basic moiety, such as, but not limited to a pyridine or imidazole, and an acidic moiety, such as, but not limited to a carboxylic acid, zwitterions ("inner salts") may be formed and are also included within the term "salt(s)" as used herein.

Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

Polymorphic forms of the compounds of Formula (I), and of the salts, solvates, esters and prodrugs of the compounds of Formula (I) are intended to be included in the present invention.

As used herein, the term "composition" is intended to encompass a product comprising the specified ingredients in the specified amounts, as well as any product which results, directly or indirectly, from combination of the specified ingredients in the specified amounts.

Therapeutic Applications

The invention provides for use of compounds and pharmaceutical compositions described herein in treating primary biliary cholangitis. The compounds are a compound of Formula (I) or a pharmaceutically acceptable salt thereof. The invention also provides methods of treating primary biliary cholangitis by administering a compound of Formula (I) or a pharmaceutically acceptable salt thereof to a subject in need thereof. In a preferred embodiment, the compound is saroglitazar magnesium salt. Various aspects and embodiments of the foregoing are described in more detail below.

Exemplary Medical Uses

One aspect of the invention provides a pharmaceutical composition comprising a compound of Formula (I) or a pharmaceutically acceptable salt thereof, for use in treating primary biliary cholangitis; wherein Formula (I) is represented by:

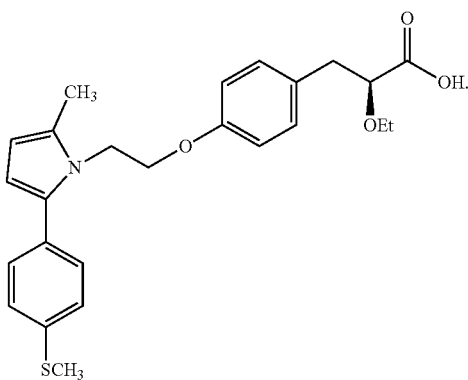

The pharmaceutical composition for use may be further characterized according to, for example, the identity of the components in the pharmaceutical composition, the route by which the pharmaceutical composition is administered to a subject, use of the pharmaceutical composition in combination with additional therapeutic agents, dosing amount of a compound of Formula (I) or pharmaceutically acceptable salt thereof, dosing frequency of the pharmaceutical composition, patients to be treated, and other features as described in more detail below.

Identity of Components in the Pharmaceutical Composition

The pharmaceutical composition for use may be further characterized according to the identity of components in the pharmaceutical composition. For example, in certain embodiments, the compound is a pharmaceutically acceptable salt of the compound of Formula (I). In certain embodiments, the compound is a metal cation salt of the compound of Formula (I). In certain embodiments, the compound is saroglitazar magnesium salt.

Saroglitazar magnesium salt is represented by:

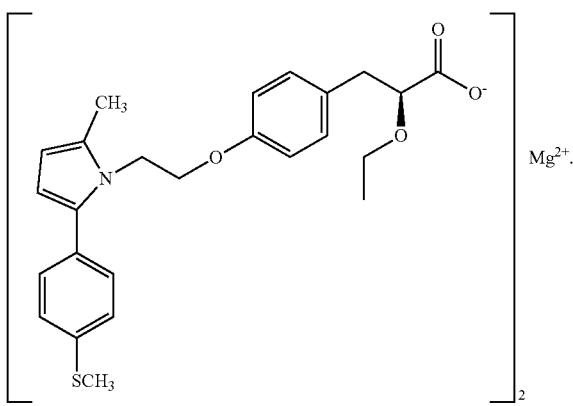

In certain other embodiments, the pharmaceutical composition further comprises one or more pharmaceutical excipients. In certain embodiments, the pharmaceutical formulation is in the form of a tablet or capsule.

Route of Administration

The pharmaceutical composition for use can be further characterized according to the route of administration for the pharmaceutical composition. For example, in certain embodiments, the composition is administered orally.

Combination Therapy

In certain other embodiments, the composition is for use in combination with at least one other therapeutic agent. In certain embodiments, the therapeutic agent is ursodeoxycholic acid or a pharmaceutically acceptable salt thereof. In certain embodiments, the therapeutic agent is obeticholic acid or a pharmaceutically acceptable salt thereof. In certain embodiments, the therapeutic agent is Pioglitazone or a pharmaceutically acceptable salt thereof.

Therapeutic Effects

The pharmaceutical composition for use can be further characterized according to therapeutic effects. For example, in certain embodiments, the use is characterized by inhibiting progression of primary biliary cholangitis.

Subjects to be Treated

The pharmaceutical composition for use can be further characterized in that its use is for administration to a particular type of subject. In certain embodiments, the composition is for administration to a human subject. In certain embodiments, the composition is for administration to an adult human. In certain other embodiments, the composition is for administration to a veterinary animal.

In yet other embodiments, the composition is for administration to a subject presenting with slow, progressive decline of small bile ducts and parallel increase in liver fibrosis. In certain other embodiments, the composition is for administration to a subject presenting with early development of liver fibrosis and liver failure. In certain other embodiments, the composition is for administration to a subject presenting with very rapid onset of ductopenia and severe icteric cholestasis that progresses to cirrhosis in less than 5 years.

In certain other embodiments, the composition is for administration to a subject having an alkaline phosphatase serum concentration of at least 160 U/L. In certain embodiments, the subject has an alkaline phosphatase serum concentration of at least 200 U/L. In certain embodiments, the subject has an alkaline phosphatase serum concentration of at least 300 U/L. In certain embodiments, the subject has an alkaline phosphatase serum concentration of at least 400 U/L, 500 U/L, 600 U/L, or 700 U/L.

In certain embodiments, the composition is for administration to a subject that is at least partially refractory to ursodeoxycholic acid or a pharmaceutically acceptable salt thereof. In certain other embodiments, the composition is for administration to a subject that is at least partially refractory to obeticholic acid or a pharmaceutically acceptable salt thereof.

Dosing Amount

In certain embodiments, composition for use can be further characterized according to the dose of compound administered to a subject. For example, in certain embodiments, the pharmaceutical composition for use is further characterized according to the feature that the pharmaceutical composition provides the compound of Formula (I) or a pharmaceutically acceptable salt thereof at a dose in the range of 0.5 mg to 5 mg with respect to saroglitazar. In certain embodiments, the compound is saroglitazar magnesium salt, and the composition is for administration to a human subject to provide saroglitazar magnesium salt at a dose of 4 mg.

In certain other embodiments, the pharmaceutical composition is administered orally in an amount to provide saroglitazar or a pharmaceutically acceptable salt thereof in the range of about 0.1 to about 10 mg on each day the pharmaceutical composition is administered to the subject. In certain other embodiments, the pharmaceutical composition is administered orally in an amount to provide saroglitazar or a pharmaceutically acceptable salt thereof in the range of about 0.1 to about 0.5 mg on each day the pharmaceutical composition is administered to the subject. In certain embodiments, the pharmaceutical composition is administered orally in an amount to provide saroglitazar or a pharmaceutically acceptable salt thereof in the range of about 0.5 to about 1.0 mg on each day the pharmaceutical composition is administered to the subject. In certain embodiments, the pharmaceutical composition is administered orally in an amount to provide saroglitazar or a pharmaceutically acceptable salt thereof in the range of about 1.0 to about 1.5 mg on each day the pharmaceutical composition is administered to the subject. In certain embodiments, the pharmaceutical composition is administered orally in an amount to provide saroglitazar or a pharmaceutically acceptable salt thereof in the range of about 1.5 to about 2.0 mg on each day the pharmaceutical composition is administered to the subject. In certain embodiments, the pharmaceutical composition is administered orally in an amount to provide saroglitazar or a pharmaceutically acceptable salt thereof in the range of about 2.0 to about 2.5 mg on each day the pharmaceutical composition is administered to the subject. In certain embodiments, the pharmaceutical composition is administered orally in an amount to provide saroglitazar or a pharmaceutically acceptable salt thereof in the range of about 2.5 to about 3.0 mg on each day the pharmaceutical composition is administered to the subject. In certain embodiments, the pharmaceutical composition is administered orally in an amount to provide saroglitazar or a pharmaceutically acceptable salt thereof in the range of about 3.0 to about 3.5 mg on each day the pharmaceutical composition is administered to the subject. In certain embodiments, the pharmaceutical composition is administered orally in an amount to provide saroglitazar or a pharmaceutically acceptable salt thereof in the range of about 3.5 to about 4.0 mg on each day the pharmaceutical composition is administered to the subject. In certain embodiments, the pharmaceutical composition is administered orally in an amount to provide saroglitazar or a pharmaceutically acceptable salt thereof in the range of about 4.0 to about 4.5 mg on each day the pharmaceutical composition is administered to the subject. In certain embodiments, the pharmaceutical composition is administered orally in an amount to provide saroglitazar or a pharmaceutically acceptable salt thereof in the range of about 4.5 to about 5.0 mg on each day the pharmaceutical composition is administered to the subject. In certain embodiments, the pharmaceutical composition is administered orally in an amount to provide saroglitazar or a pharmaceutically acceptable salt thereof in the range of about 1.75 to about 2.25 mg on each day the pharmaceutical composition is administered to the subject. In certain embodiments, the pharmaceutical composition is administered orally in an amount to provide saroglitazar or a pharmaceutically acceptable salt thereof in the range of about 3.75 to about 4.25 mg on each day the pharmaceutical composition is administered to the subject. In certain embodiments, the compound is a pharmaceutically acceptable salt of saroglitazar, and the pharmaceutical composition is administered orally to provide the pharmaceutically acceptable salt of saroglitazar in an amount of about 2.0 mg on each day the pharmaceutical composition is administered to the subject. In certain embodiments, the compound is a pharmaceutically acceptable salt of saroglitazar, and the pharmaceutical composition is administered orally to provide the pharmaceutically acceptable salt of saroglitazar in an amount of about 4.0 mg on each day the pharmaceutical composition is administered to the subject.

In certain other embodiments, the pharmaceutical composition is administered orally in an amount to provide saroglitazar or a pharmaceutically acceptable salt thereof in the range of about 0.1 to about 1 mg, about 1 to about 2 mg, about 2 to about 3 mg, about 3 to about 4 mg, about 4 to about 5 mg, about 5 to about 6 mg, about 6 to about 7 mg, about 8 to about 9 mg, or about 9 to about 10 mg, on each day the pharmaceutical composition is administered to the subject.

Dosing Schedule

The method may be further characterized according to a dosing schedule by which the pharmaceutical composition is be administered to the subject. For example, in certain embodiments, the pharmaceutical composition is administered to the subject in the morning prior to the subject consuming food.

In certain other embodiments, the pharmaceutical composition is administered to the subject once daily. In yet other embodiments, the pharmaceutical composition is administered to the subject once daily for at least 1 week. In yet other embodiments, the pharmaceutical composition is administered to the subject once daily for at least 2 weeks. In yet other embodiments, the pharmaceutical composition is administered to the subject once daily for at least 3 weeks. In yet other embodiments, the pharmaceutical composition is administered to the subject once daily for at least 4 weeks. In yet other embodiments, the pharmaceutical composition is administered to the subject once daily for at least 6 weeks. In yet other embodiments, the pharmaceutical composition is administered to the subject once daily for at least 8 weeks. In yet other embodiments, the pharmaceutical composition is administered to the subject once daily for at least 10 weeks. In yet other embodiments, the pharmaceutical composition is administered to the subject once daily for at least 12 weeks. In yet other embodiments, the pharmaceutical composition is administered to the subject once daily for at least 14 weeks. In yet other embodiments, the pharmaceutical composition is administered to the subject once daily for at least 16 weeks.

Reduction in the Amount of Bile in Liver of Subject

The pharmaceutical composition for use may be further characterized according to a reduction in the amount of bile in a liver of the subject. For example, in certain embodiments, there is a reduction in the amount of bile in the liver of the subject. In certain embodiments, there is at least a 5% w/w reduction in the amount of bile in the liver of the subject. In certain embodiments, there is at least a 10% w/w reduction in the amount of bile in the liver of the subject. In certain embodiments, there is at least a 15% w/w reduction in the amount of bile in the liver of the subject. In certain embodiments, there is at least a 20% w/w reduction in the amount of bile in the liver of the subject. In certain embodiments, there is at least a 25% w/w reduction in the amount of bile in the liver of the subject. In certain embodiments, there is at least a 30% w/w reduction in the amount of bile in the liver of the subject. In certain embodiments, there is at least a 40% w/w reduction in the amount of bile in the liver of the subject. In certain embodiments, there is at least a 50% w/w reduction in the amount of bile in the liver of the subject. In certain embodiments, there is at least a 60% w/w reduction in the amount of bile in the liver of the subject. In certain embodiments, there is at least a 70% w/w reduction in the amount of bile in the liver of the subject. In certain embodiments, there is at least a 80% w/w reduction in the amount of bile in the liver of the subject. In certain embodiments, there is at least a 90% w/w reduction in the amount of bile in the liver of the subject.

Reduction in Concentration of Alkaline Phosphatase in the Serum of the Subject

The pharmaceutical composition for use may be further characterized according to a reduction in the concentration of alkaline phosphatase in the serum of a subject due to administering the pharmaceutical composition to the subject. For example, in certain embodiments, there is a reduction in the concentration of alkaline phosphatase in the serum of the subject. In certain embodiments, there is at least a 5% reduction in the U/L concentration of alkaline phosphatase in the serum of the subject. In certain embodiments, there is at least a 10% reduction in the U/L concentration of alkaline phosphatase in the serum of the subject. In certain embodiments, there is at least a 15% reduction in the U/L concentration of alkaline phosphatase in the serum of the subject. In certain embodiments, there is at least a 20% reduction in the U/L concentration of alkaline phosphatase in the serum of the subject. In certain embodiments, there is at least a 25% reduction in the U/L concentration of alkaline phosphatase in the serum of the subject. In certain embodiments, there is at least a 30% reduction in the U/L concentration of alkaline phosphatase in the serum of the subject. In certain embodiments, there is at least a 40% reduction in the U/L concentration of alkaline phosphatase in the serum of the subject. In certain embodiments, there is at least a 50% reduction in the U/L concentration of alkaline phosphatase in the serum of the subject. In certain embodiments, there is at least a 60% reduction in the U/L concentration of alkaline phosphatase in the serum of the subject. In certain embodiments, there is at least a 70% reduction in the U/L concentration of alkaline phosphatase in the serum of the subject. In certain embodiments, there is at least a 80% reduction in the U/L concentration of alkaline phosphatase in the serum of the subject. In certain embodiments, there is at least a 90% reduction in the U/L concentration of alkaline phosphatase in the serum of the subject.

Reduction in Concentration of Anti-Mitochondrial Antibodies in the Serum of the Subject The pharmaceutical composition for use may be further characterized according to a reduction in the concentration of anti-mitochondrial antibodies in the serum of a subject due to administration of the pharmaceutical composition. For example, in certain embodiments, there is a reduction in the concentration of anti-mitochondrial antibodies in the serum of the subject. In certain embodiments, there is at least a 5% reduction in the concentration of anti-mitochondrial antibodies in the serum of the subject. In certain embodiments, there is at least a 10% reduction in the concentration of anti-mitochondrial antibodies in the serum of the subject. In certain embodiments, there is at least a 15% reduction in the concentration of anti-mitochondrial antibodies in the serum of the subject. In certain embodiments, there is at least a 20% reduction in the concentration of anti-mitochondrial antibodies in the serum of the subject. In certain embodiments, there is at least a 25% reduction in the concentration of anti-mitochondrial antibodies in the serum of the subject. In certain embodiments, there is at least a 30% reduction in the concentration of anti-mitochondrial antibodies in the serum of the subject. In certain embodiments, there is at least a 40% reduction in the concentration of anti-mitochondrial antibodies in the serum of the subject. In certain embodiments, there is at least a 50% reduction in the concentration of anti-mitochondrial antibodies in the serum of the subject. In certain embodiments, there is at least a 60% reduction in the concentration of anti-mitochondrial antibodies in the serum of the subject. In certain embodiments, there is at least a 70% reduction in the concentration of anti-mitochondrial antibodies in the serum of the subject. In certain embodiments, there is at least a 80% reduction in the concentration of anti-mitochondrial antibodies in the serum of the subject. In certain embodiments, there is at least a 90% reduction in the concentration of anti-mitochondrial antibodies in the serum of the subject.

Reduction in the Amount of Inflammation in the Liver of the Subject

The pharmaceutical composition for use may be further characterized according to a reduction in the amount of inflammation in the liver of the subject due administration of the pharmaceutical composition. For example, in certain embodiments, there is a reduction in the amount of inflammation in the liver of the subject. In certain embodiments, there is at least a 5% reduction in the amount of inflammation in the liver of the subject. In certain embodiments, there is at least a 10% reduction in the amount of inflammation in the liver of the subject. In certain embodiments, there is at least a 15% reduction in the amount of inflammation in the liver of the subject. In certain embodiments, there is at least a 20% reduction in the amount of inflammation in the liver of the subject. In certain embodiments, there is at least a 25% reduction in the amount of inflammation in the liver of the subject. In certain embodiments, there is at least a 30% reduction in the amount of inflammation in the liver of the subject. In certain embodiments, there is at least a 40% reduction in the amount of inflammation in the liver of the subject. In certain embodiments, there is at least a 50% reduction in the amount of inflammation in the liver of the subject. In certain embodiments, there is at least a 60% reduction in the amount of inflammation in the liver of the subject. In certain embodiments, there is at least a 70% reduction in the amount of inflammation in the liver of the subject. In certain embodiments, there is at least a 80% reduction in the amount of inflammation in the liver of the subject. In certain embodiments, there is at least a 90% reduction in the amount of inflammation in the liver of the subject.

Reduction in the Amount of any Scarring in the Liver of the Subject

The pharmaceutical composition for use may be further characterized according to a reduction in the amount of any scarring in the liver of the subject due to administration of the pharmaceutical composition. For example, in certain embodiments, there is a reduction in the amount of any scarring in the liver of the subject. In certain embodiments, there is at least a 5% by volume reduction in the amount of scarring in the liver of the subject. In certain embodiments, there is at least a 10% by volume reduction in the amount of scarring in the liver of the subject. In certain embodiments, there is at least a 15% by volume reduction in the amount of scarring in the liver of the subject. In certain embodiments, there is at least a 20% by volume reduction in the amount of scarring in the liver of the subject. In certain embodiments, there is at least a 25% by volume reduction in the amount of scarring in the liver of the subject. In certain embodiments, there is at least a 30% by volume reduction in the amount of scarring in the liver of the subject. In certain embodiments, there is at least a 40% by volume reduction in the amount of scarring in the liver of the subject. In certain embodiments, there is at least a 50% by volume reduction in the amount of scarring in the liver of the subject. In certain embodiments, there is at least a 60% by volume reduction in the amount of scarring in the liver of the subject. In certain embodiments, there is at least a 70% by volume reduction in the amount of scarring in the liver of the subject. In certain embodiments, there is at least a 80% by volume reduction in the amount of scarring in the liver of the subject. In certain embodiments, there is at least a 90% by volume reduction in the amount of scarring in the liver of the subject.

Duration of Effect

The pharmaceutical composition for use may be further characterized according to the duration of effect provided, such as duration of reduction in the amount of any scarring in the liver of the subject. For example, in certain embodiments, there is a reduction for a duration of at least 3 days after the last administration of the compound. In certain embodiments, there is a reduction for a duration of at least 5 days after the last administration of the compound. In certain embodiments, there is a reduction for a duration of at least 1 week after the last administration of the compound. In certain embodiments, there is a reduction for a duration of at least 2 weeks after the last administration of the compound. In certain embodiments, there is a reduction for a duration of at least 3 weeks after the last administration of the compound. In certain embodiments, there is a reduction for a duration of at least 4 weeks after the last administration of the compound. In certain embodiments, there is a reduction for a duration of at least 5 weeks after the last administration of the compound.

Exemplary Therapeutic Methods

Another aspect of the invention provides a method of treating primary biliary cholangitis. The method comprises administering to a subject in need thereof an effective amount of a compound of Formula (I) or a pharmaceutically acceptable salt thereof, to treat the primary biliary cholangitis; wherein Formula (I) is represented by:

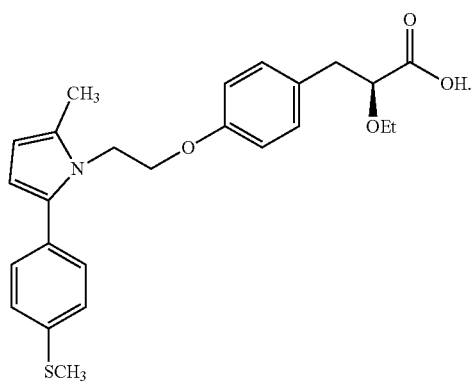

The method may be further characterized according to, for example, the identity of the compound administered to the patient, the route by which the compound is administered to the patient, administration of additional therapeutic agents, dosing amount of a compound of Formula (I) or pharmaceutically acceptable salt thereof, dosing frequency of a compound of Formula (I) or pharmaceutically acceptable salt thereof, patients to be treated, and other features as described in more detail below.

Identity of Compound to be Administered

The method may be further characterized according to the identity of the compound administered to the patient. In certain embodiments, the compound is a pharmaceutically acceptable salt of the compound of Formula (I). In certain embodiments, the compound is a metal cation salt of the compound of Formula (I). In certain embodiments, the compound is saroglitazar magnesium salt.

Saroglitazar magnesium salt is represented by:

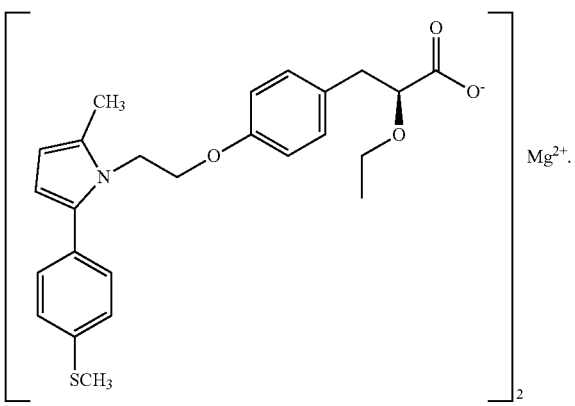

Route of Administration

The method may be further characterized according to the route by which the compound is administered to the patient. For example, in certain embodiments, the compound is administered orally to the subject.

Active Ingredient Formulated as a Pharmaceutical Formulation

The method may be further characterized according to the compound of Formula (I) or pharmaceutically acceptable salt thereof being formulated as a pharmaceutical formulation for administration to a subject. For example, in certain embodiments, the compound is administered in the form of a pharmaceutical formulation. In certain embodiments, the compound is administered in the form of a pharmaceutical formulation containing one or more pharmaceutical excipients. In certain embodiments, the pharmaceutical formulation is in the form of a tablet or capsule.

Aspects of Therapeutic Impact

The method may be further characterized according to aspects of the therapeutic impact of administering the compound of Formula (I) or a pharmaceutically acceptable salt thereof. For example, in certain embodiments, the administering inhibits progression of primary biliary cholangitis in the subject.

Combination Therapy

The method may be further characterized according to whether one or more other therapeutic agents are administered to the patient in support of treating primary biliary cholangitis. For example, in certain embodiments, the method further comprises administering to the subject at least one other therapeutic agent. In certain embodiments, the therapeutic agent is ursodeoxycholic acid or a pharmaceutically acceptable salt thereof. In certain embodiments, the therapeutic agent is obeticholic acid or a pharmaceutically acceptable salt thereof.

Subjects to be Treated

The method may be further characterized according to the identity of subjects to be treated. For example, in certain embodiments, the subject is a human. In certain embodiments, the subject is an adult human. In certain embodiments, the subject is a veterinary animal.

In certain other embodiments, the subject presents with slow, progressive decline of small bile ducts and parallel increase in liver fibrosis. In certain other embodiments, the subject presents with early development of liver fibrosis and liver failure. In certain other embodiments, the subject presents with very rapid onset of ductopenia and severe icteric cholestasis that progresses to cirrhosis in less than 5 years.

In certain embodiments, the subject has an alkaline phosphatase serum concentration of at least 160 U/L. In certain embodiments, the subject has an alkaline phosphatase serum concentration of at least 200 U/L. In certain embodiments, the subject has an alkaline phosphatase serum concentration of at least 300 U/L. In certain embodiments, the subject has an alkaline phosphatase serum concentration of at least 400 U/L, 500 U/L, 600 U/L, or 700 U/L.

In certain embodiments, the subject is at least partially refractory to ursodeoxycholic acid or a pharmaceutically acceptable salt thereof. In certain embodiments, the subject is at least partially refractory to obeticholic acid or a pharmaceutically acceptable salt thereof.

Dose of Compound to be Administered to the Subject

The method may be further characterized according to the dose compound to be administered to the subject. For example, in certain embodiments, the compound is administered at a dose in the range of 0.5 mg to 5 mg with respect to saroglitazar.

In certain other embodiments, the compound is saroglitazar magnesium salt, which is administered to the subject at a 4 mg dose, wherein the subject is a human.

In certain other embodiments, the compound is administered orally in an amount to provide saroglitazar or a pharmaceutically acceptable salt thereof in the range of about 0.1 to about 10 mg on each day the compound is administered to the subject. For example, in certain embodiments, the compound is administered orally in an amount to provide saroglitazar or a pharmaceutically acceptable salt thereof in the range of about 0.1 to about 0.5 mg on each day the compound is administered to the subject. In certain embodiments, the compound is administered orally in an amount to provide saroglitazar or a pharmaceutically acceptable salt thereof in the range of about 0.5 to about 1.0 mg on each day the compound is administered to the subject. In certain embodiments, the compound is administered orally in an amount to provide saroglitazar or a pharmaceutically acceptable salt thereof in the range of about 1.0 to about 1.5 mg on each day the compound is administered to the subject. In certain embodiments, the compound is administered orally in an amount to provide saroglitazar or a pharmaceutically acceptable salt thereof in the range of about 1.5 to about 2.0 mg on each day the compound is administered to the subject. In certain embodiments, the compound is administered orally in an amount to provide saroglitazar or a pharmaceutically acceptable salt thereof in the range of about 2.0 to about 2.5 mg on each day the compound is administered to the subject. In certain embodiments, the compound is administered orally in an amount to provide saroglitazar or a pharmaceutically acceptable salt thereof in the range of about 2.5 to about 3.0 mg on each day the compound is administered to the subject. In certain embodiments, the compound is administered orally in an amount to provide saroglitazar or a pharmaceutically acceptable salt thereof in the range of about 3.0 to about 3.5 mg on each day the compound is administered to the subject. In certain embodiments, the compound is administered orally in an amount to provide saroglitazar or a pharmaceutically acceptable salt thereof in the range of about 3.5 to about 4.0 mg on each day the compound is administered to the subject. In certain embodiments, the compound is administered orally in an amount to provide saroglitazar or a pharmaceutically acceptable salt thereof in the range of about 4.0 to about 4.5 mg on each day the compound is administered to the subject. In certain embodiments, the compound is administered orally in an amount to provide saroglitazar or a pharmaceutically acceptable salt thereof in the range of about 4.5 to about 5.0 mg on each day the compound is administered to the subject. In certain embodiments, the compound is administered orally in an amount to provide saroglitazar or a pharmaceutically acceptable salt thereof in the range of about 1.75 to about 2.25 mg on each day the compound is administered to the subject. In certain embodiments, the compound is administered orally in an amount to provide saroglitazar or a pharmaceutically acceptable salt thereof in the range of about 3.75 to about 4.25 mg on each day the compound is administered to the subject. In certain embodiments, the compound is a pharmaceutically acceptable salt of saroglitazar, and said pharmaceutically acceptable salt of saroglitazar is administered orally in an amount of about 2.0 mg on each day the compound is administered to the subject. In certain embodiments, the compound is a pharmaceutically acceptable salt of saroglitazar, and said pharmaceutically acceptable salt of saroglitazar is administered orally in an amount of about 4.0 mg on each day the compound is administered to the subject.

In certain other embodiments, the compound is administered orally in an amount to provide saroglitazar or a pharmaceutically acceptable salt thereof in the range of about 0.1 to about 1 mg, about 1 to about 2 mg, about 2 to about 3 mg, about 3 to about 4 mg, about 4 to about 5 mg, about 5 to about 6 mg, about 6 to about 7 mg, about 8 to about 9 mg, or about 9 to about 10 mg, on each day the compound is administered to the subject.

Dosing Schedule

The method may be further characterized according to a dosing schedule by which the compound of Formula (I) or a pharmaceutically acceptable salt thereof may be administered to the subject. For example, in certain embodiments, the compound is administered to the subject in the morning prior to the subject consuming food.

In certain other embodiments, the compound is administered to the subject once daily. In yet other embodiments, the compound is administered to the subject once daily for at least 1 week. In yet other embodiments, the compound is administered to the subject once daily for at least 2 weeks. In yet other embodiments, the compound is administered to the subject once daily for at least 3 weeks. In yet other embodiments, the compound is administered to the subject once daily for at least 4 weeks. In yet other embodiments, the compound is administered to the subject once daily for at least 6 weeks. In yet other embodiments, the compound is administered to the subject once daily for at least 8 weeks. In yet other embodiments, the compound is administered to the subject once daily for at least 10 weeks. In yet other embodiments, the compound is administered to the subject once daily for at least 12 weeks. In yet other embodiments, the compound is administered to the subject once daily for at least 14 weeks. In yet other embodiments, the compound is administered to the subject once daily for at least 16 weeks.

Reduction in the Amount of Bile in Liver of Subject

The method may be further characterized according to a reduction in the amount of bile in a liver of a subject due to the therapeutic method (e.g., administering a compound of Formula I or a pharmaceutically acceptable salt thereof to the subject). For example, in certain embodiments, the method achieves a reduction in the amount of bile in the liver of the subject. In certain embodiments, the method achieves at least a 5% w/w reduction in the amount of bile in the liver of the subject. In certain embodiments, the method achieves at least a 10% w/w reduction in the amount of bile in the liver of the subject. In certain embodiments, the method achieves at least a 15% w/w reduction in the amount of bile in the liver of the subject. In certain embodiments, the method achieves at least a 20% w/w reduction in the amount of bile in the liver of the subject. In certain embodiments, the method achieves at least a 25% w/w reduction in the amount of bile in the liver of the subject. In certain embodiments, the method achieves at least a 30% w/w reduction in the amount of bile in the liver of the subject. In certain embodiments, the method achieves at least a 40% w/w reduction in the amount of bile in the liver of the subject. In certain embodiments, the method achieves at least a 50% w/w reduction in the amount of bile in the liver of the subject. In certain embodiments, the method achieves at least a 60% w/w reduction in the amount of bile in the liver of the subject. In certain embodiments, the method achieves at least a 70% w/w reduction in the amount of bile in the liver of the subject. In certain embodiments, the method achieves at least a 80% w/w reduction in the amount of bile in the liver of the subject. In certain embodiments, the method achieves at least a 90% w/w reduction in the amount of bile in the liver of the subject.

Reduction in Concentration of Alkaline Phosphatase in the Serum of the Subject

The method may be further characterized according to a reduction in the concentration of alkaline phosphatase in the serum of a subject due to the therapeutic method (e.g., administering a compound of Formula (I) or a pharmaceutically acceptable salt thereof to the subject). For example, in certain embodiments, the method achieves a reduction in the concentration of alkaline phosphatase in the serum of the subject. In certain embodiments, the method achieves at least a 5% reduction in the U/L concentration of alkaline phosphatase in the serum of the subject. In certain embodiments, the method achieves at least a 10% reduction in the U/L concentration of alkaline phosphatase in the serum of the subject. In certain embodiments, the method achieves at least a 15% reduction in the U/L concentration of alkaline phosphatase in the serum of the subject. In certain embodiments, the method achieves at least a 20% reduction in the U/L concentration of alkaline phosphatase in the serum of the subject. In certain embodiments, the method achieves at least a 25% reduction in the U/L concentration of alkaline phosphatase in the serum of the subject. In certain embodiments, the method achieves at least a 30% reduction in the U/L concentration of alkaline phosphatase in the serum of the subject. In certain embodiments, the method achieves at least a 40% reduction in the U/L concentration of alkaline phosphatase in the serum of the subject. In certain embodiments, the method achieves at least a 50% reduction in the U/L concentration of alkaline phosphatase in the serum of the subject. In certain embodiments, the method achieves at least a 60% reduction in the U/L concentration of alkaline phosphatase in the serum of the subject. In certain embodiments, the method achieves at least a 70% reduction in the U/L concentration of alkaline phosphatase in the serum of the subject. In certain embodiments, the method achieves at least a 80% reduction in the U/L concentration of alkaline phosphatase in the serum of the subject. In certain embodiments, the method achieves at least a 90% reduction in the U/L concentration of alkaline phosphatase in the serum of the subject.

Reduction in Concentration of Anti-Mitochondrial Antibodies in the Serum of the Subject The method may be further characterized according to a reduction in the concentration of anti-mitochondrial antibodies in the serum of a subject due to the therapeutic method (e.g., administering a compound of Formula (I) or a pharmaceutically acceptable salt thereof to the subject). For example, in certain embodiments, the method achieves a reduction in the concentration of anti-mitochondrial antibodies in the serum of the subject. In certain embodiments, the method achieves at least a 5% reduction in the concentration of anti-mitochondrial antibodies in the serum of the subject. In certain embodiments, the method achieves at least a 10% reduction in the concentration of anti-mitochondrial antibodies in the serum of the subject. In certain embodiments, the method achieves at least a 15% reduction in the concentration of anti-mitochondrial antibodies in the serum of the subject. In certain embodiments, the method achieves at least a 20% reduction in the concentration of anti-mitochondrial antibodies in the serum of the subject. In certain embodiments, the method achieves at least a 25% reduction in the concentration of anti-mitochondrial antibodies in the serum of the subject. In certain embodiments, the method achieves at least a 30% reduction in the concentration of anti-mitochondrial antibodies in the serum of the subject. In certain embodiments, the method achieves at least a 40% reduction in the concentration of anti-mitochondrial antibodies in the serum of the subject. In certain embodiments, the method achieves at least a 50% reduction in the concentration of anti-mitochondrial antibodies in the serum of the subject. In certain embodiments, the method achieves at least a 60% reduction in the concentration of anti-mitochondrial antibodies in the serum of the subject. In certain embodiments, the method achieves at least a 70% reduction in the concentration of anti-mitochondrial antibodies in the serum of the subject. In certain embodiments, the method achieves at least a 80% reduction in the concentration of anti-mitochondrial antibodies in the serum of the subject. In certain embodiments, the method achieves at least a 90% reduction in the concentration of anti-mitochondrial antibodies in the serum of the subject.

Reduction in the Amount of Inflammation in the Liver of the Subject

The method may be further characterized according to a reduction in the amount of inflammation in the liver of the subject due to the therapeutic method (e.g., administering a compound of Formula (I) or a pharmaceutically acceptable salt thereof to the subject). For example, in certain embodiments, the method achieves a reduction in the amount of inflammation in the liver of the subject. In certain embodiments, the method achieves at least a 5% reduction in the amount of inflammation in the liver of the subject. In certain embodiments, the method achieves at least a 10% reduction in the amount of inflammation in the liver of the subject. In certain embodiments, the method achieves at least a 15% reduction in the amount of inflammation in the liver of the subject. In certain embodiments, the method achieves at least a 20% reduction in the amount of inflammation in the liver of the subject. In certain embodiments, the method achieves at least a 25% reduction in the amount of inflammation in the liver of the subject. In certain embodiments, the method achieves at least a 30% reduction in the amount of inflammation in the liver of the subject. In certain embodiments, the method achieves at least a 40% reduction in the amount of inflammation in the liver of the subject. In certain embodiments, the method achieves at least a 50% reduction in the amount of inflammation in the liver of the subject. In certain embodiments, the method achieves at least a 60% reduction in the amount of inflammation in the liver of the subject. In certain embodiments, the method achieves at least a 70% reduction in the amount of inflammation in the liver of the subject. In certain embodiments, the method achieves at least a 80% reduction in the amount of inflammation in the liver of the subject. In certain embodiments, the method achieves at least a 90% reduction in the amount of inflammation in the liver of the subject.

Reduction in the Amount of any Scarring in the Liver of the Subject

The method may be further characterized according to a reduction in the amount of any scarring in the liver of the subject due to the therapeutic method (e.g., administering a compound of Formula I or a pharmaceutically acceptable salt thereof to the subject). For example, in certain embodiments, the method achieves a reduction in the amount of any scarring in the liver of the subject. In certain embodiments, the method achieves at least a 5% by volume reduction in the amount of scarring in the liver of the subject. In certain embodiments, the method achieves at least a 10% by volume reduction in the amount of scarring in the liver of the subject. In certain embodiments, the method achieves at least a 15% by volume reduction in the amount of scarring in the liver of the subject. In certain embodiments, the method achieves at least a 20% by volume reduction in the amount of scarring in the liver of the subject. In certain embodiments, the method achieves at least a 25% by volume reduction in the amount of scarring in the liver of the subject. In certain embodiments, the method achieves at least a 30% by volume reduction in the amount of scarring in the liver of the subject. In certain embodiments, the method achieves at least a 40% by volume reduction in the amount of scarring in the liver of the subject. In certain embodiments, the method achieves at least a 50% by volume reduction in the amount of scarring in the liver of the subject. In certain embodiments, the method achieves at least a 60% by volume reduction in the amount of scarring in the liver of the subject. In certain embodiments, the method achieves at least a 70% by volume reduction in the amount of scarring in the liver of the subject. In certain embodiments, the method achieves at least a 80% by volume reduction in the amount of scarring in the liver of the subject. In certain embodiments, the method achieves at least a 90% by volume reduction in the amount of scarring in the liver of the subject.

Duration of Effect

The method may be further characterized according to the duration of effect provided by the therapeutic method, such as duration of reduction in the amount of any scarring in the liver of the subject due to the therapeutic method (e.g., administering a compound of Formula (I) or a pharmaceutically acceptable salt thereof to the subject). For example, in certain embodiments, the method achieves said reduction for a duration of at least 3 days after the last administration of the compound. In certain embodiments, the method achieves said reduction for a duration of at least 5 days after the last administration of the compound. In certain embodiments, the method achieves said reduction for a duration of at least 1 week after the last administration of the compound. In certain embodiments, the method achieves said reduction for a duration of at least 2 weeks after the last administration of the compound. In certain embodiments, the method achieves said reduction for a duration of at least 3 weeks after the last administration of the compound. In certain embodiments, the method achieves said reduction for a duration of at least 4 weeks after the last administration of the compound. In certain embodiments, the method achieves said reduction for a duration of at least 5 weeks after the last administration of the compound.

Pharmaceutical Compositions

Another aspect of the invention provides pharmaceutical compositions. In certain embodiments, the pharmaceutical composition comprises a compound described herein (e.g., a compound of Formula (I) or a pharmaceutically acceptable salt thereof) and one or more pharmaceutical excipients.

In certain embodiments, the present invention provides a suitable pharmaceutical composition of compounds of formula (I) or their derivatives, which comprises one or more pharmaceutical excipients, antioxidants and chelating agents, wherein the pH of the composition is above 6, preferably in the range from about pH 6 to pH of about 10.

In such embodiments the pharmaceutical composition of the present invention essentially comprises of
 the pharmaceutically active substance;
 Suitable additives;
 a suitable stabilizer;
 optionally with one or more pharmaceutically acceptable excipients.

In an embodiment suitable stabilizers may be selected from the classes of antioxidants or chelating agents.

In an embodiment the pharmaceutical excipients according to the present invention can be selected from solubilizers, diluents, fillers, disintegrants, binder, lubricants, glidants, wetting agents, solvents and the like as is known in the art.

In embodiment suitable additives are selected from sodium benzoate, sodium hydroxide, sodium sulfite and sodium carbonate.

In an embodiment antioxidants used according to the present invention include, but are not limited to citric acid, alpha tocopherol, sodium sulphite, sodium metabisulphite, butylated hydroxy anisole (BHA), BHT (2,6-di-tert-butyl-4-methylphenol), monothioglycerol, Vitamin C (ascorbic acid), and propyl gallate and combinations thereof and other similar material known to those of ordinary skilled in the art.

Chelating agent used according to the present invention include, but are not limited to Disodium EDTA, citric acid and or its salts, maleic acid, chlorambutol, chlorhexidine or its salts, chlorocresol, combinations thereof and other similar material known to those of ordinary skill in the art.

As used herein, the term "binders" is intended to mean substances used to cause adhesion of powder particles in tablet granulations. Such compounds include, by way of example and without limitation, acacia alginic acid, tragacanth, carboxymethylcellulose sodium, poly (vinylpyrrolidone), compressible sugar (e.g., NuTab), ethylcellulose, gelatin, liquid glucose, methyl cellulose, povidone and pregelatinized starch, combinations thereof and other similar material known to those of ordinary skill in the art.

When needed, other binders may also be included in the present invention. Exemplary binders include starch, poly (ethylene glycol), guar gum, polysaccharide, bentonites, sugars, invert sugars, poloxamers (PLURONIC F68, PLURONIC F127), collagen, albumin, celluloses in non-aqueous solvents, and the like or their suitable combinations. Other binders which may be included may be, for example, poly(propylene glycol), polyoxyethylene-polypropylene copolymer, polyethylene ester, polyethylene sorbitan ester, poly(ethylene oxide), microcrystalline cellulose, poly(vinylpyrrolidone), combinations thereof and other such materials known to those of ordinary skill in the art. As used herein, the term "diluent" or "filler" is intended to mean inert substances used as fillers to create the desired bulk, flow properties, and compression characteristics in the preparation of tablets and capsules. Such compounds include, by way of example and without limitation, dibasic calcium phosphate, kaolin, sucrose, mannitol, microcrystalline cellulose, powdered cellulose, precipitated calcium carbonate, sorbitol, starch, combinations thereof and other such materials known to those of ordinary skill in the art.

As used herein, the term "glidant" is intended to mean agents used in tablet and capsule formulations to improve flow-properties during tablet compression and to produce an anti-caking effect. Such compounds include, by way of example and without limitation, colloidal silica, calcium silicate, magnesium silicate, silicon hydrogel, cornstarch, talc, combinations thereof and other such materials known to those of ordinary skill in the art.

In an embodiment, the term "lubricant" is intended to mean substances used in tablet formulations to reduce friction during tablet compression. Such compounds include, by way of example and without limitation, calcium stearate, magnesium stearate, mineral oil, stearic acid, zinc stearate, suitable combinations thereof and other such materials known to those of ordinary skill in the art.

In an embodiment, the term "disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starched thereof, sweeteners, clays, such as bentonite, microcrystalline cellulose (e.g. Avicel™), carsium (e.g. Amberlite™), alginates, sodium starch glycolate, gums such as agar, guar, locust bean, karaya, pectin, tragacanth, combinations thereof and other such materials known to those of ordinary skill in the art.

In an embodiment, the term "wetting agent" is intended to mean a compound used to aid in attaining intimate contact between solid particles and liquids. Exemplary wetting agents include, by way of example and without limitation, poloxamers, gelatin, casein, Glycerol mono-oleate, lecithin (phosphatides), gum acacia, cholesterol, tragacanth, stearic acid, benzalkonium chloride, calcium stearate, glycerol monostearate, cetostearyl alcohol, sodium lauryl sulphate, sodium dodecyl sulfate, salts of bile acids (taurocholate, glycocholate, cholate, deoxycholate, etc.), cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters, (e.g., TWEEN), polyethylene glycols, polyoxyethylene stearates colloidal silicon dioxide, phosphates, sodium dodecylsulfate, carboxymethylcellulose calcium, carboxy methylcellulose sodium, methyl cellulose, hydroxyethylcellulose, hydroxylpropylcellulose, hydroxy propyl methyl cellulose phthalate, noncrystalline cellulose, magnesium aluminum silicate, triethanolamine, polyvinyl alcohol, and poly vinyl pyrrolidone (PVP) & their suitable combinations and other such materials known to those of ordinary skill in the art. Tyloxapol (a nonionic liquid polymer of the alkyl aryl polyether alcohol type, also known as superinone or triton) is another useful wetting agent which may be used. The stable pharmaceutical composition according to the present invention may be in the form of tablet or capsule or a powder or a suspension in a liquid or an aerosol formulation or solutions, preferably in the form of tablet or capsule.

In another embodiment of the present invention, is a described process for the preparation of a stable pharmaceutical composition of compounds of formula (I) or their derivatives.

The stable pharmaceutical composition may be made by direct compression, wet granulation or dry granulation methods by techniques known to persons skilled in the art. Thus, for example, In wet granulation process, the drug is mixed with one or more pharmaceutical excipients and granulated with suitable binding solution as described earlier, to form wet granules, the wet granules are dried and optionally sieved. The dried granules are mixed with one or more suitable excipients from those described elsewhere and then compressed into tablets or filled into capsules.

In direct compression process, the drug is mixed with all the pharmaceutical excipients required and then is either compressed into tablets or filled in capsules.

In dry granulation process the drug is mixed with one or more pharmaceutical excipients and compressed into slugs and these slugs are passed through required sieve. The sieved granules are mixed with one or more suitable excipients from those described elsewhere and then compressed into tablets or filled into capsules.

One or more solvents used in the formulation are selected from acetone, chloroform, dichloromethane, ethyl alcohol, ethyl acetate, methyl alcohol, isopropyl alcohol and combinations thereof and other such materials known to those of ordinary skill in the art.

Further Exemplary Dosing Regimens

In an embodiment, the compound of formula (I) or its pharmaceutically acceptable salts as defined herein or pharmaceutical compositions containing the compound of formula (I) is given to a subject in need thereof at a dose of about 0.5 mg to 5 g. A skilled person is aware how to decide the optimum dose based on the patient profile, the severity of disease, the presence of secondary medicines and the like.

Further Exemplary Treatment Regimens and Combination Therapy

In an embodiment, the compound according to formula (I) or its pharmaceutically acceptable salts can be used alone or in combination e.g., as an adjunct therapy, with at least one other therapeutic agent. Compounds according to formula (I) or its pharmaceutically acceptable salts can be given to a subject with PBC alone, or can be co-administered with a therapeutic agent including, but not limited to Ursodeoxycholic acid (UDCA) and its various derivatives and functional equivalents, Obeticholic acid (OCA), an FXR agonists such as those disclosed in WO2016127019, an agent used to control blood glucose levels, an agent used to control lipid levels, e.g., an agent used to lower or control cholesterol, an antioxidant, an appetite suppressing agent, an anti-obesity agent, to control blood glucose levels, such as, sulfonylureas, an antibiotic/probiotic or an anti-inflammatory agent. Examples of such agents are listed herein and includes chlorpropamide, glipizide, glyburide, and glimepiride; meglitinides, such as, repaglinide and nateglinide; biguanides, such as, metformin and acarbose; thiazolidinediones, such as, rosiglitazone, and pioglitazone; and insulin and its derivatives, such as, pramlintide, exenatide, humalog, novolog, humulin, novolin, ultralente, and lanrus; an agent used to control lipid levels, such as, vytorin, Clofibrate and Gemfibrozil, a plasma HDL-raising agent, a cholesterol lowering agent, a cholesterol biosynthesis inhibitor, for example an HMG-CoA reductase inhibitor (such as a statin, such as, Atorvastatin, Fluvastatin, Lovastatin, Pravastatin, Rosuvastatin, Simvastatin); an HMG-CoA synthase inhibitor, an acyl-coenzyme A: cholesterol acyltransferase (ACAT) inhibitor, such as, melinamide; probucol, niacin (nicotinic acid, Vitamin-B-3), nicotinic acid and the salts thereof and niacinamide; a cholesterol absorption inhibitor such as ezetimibe; a bile acid sequestrant, such as, cholestyramine, colestipol, and Colesevelam; fibrates such as clofibrate, fenofibrate, and gemfibrizol, vitamin B6 (also known as pyridoxine) and physiologically acceptable salts thereof, such as the HCl salt; vitamin B12 (also known as cyanocobalamin), and angiotensin II antagonist converting enzyme inhibitor; a beta-blocker; an agent used to reduce weight or suppress appetite, such as, sibutramine, orlistat and the like.

Additional Features

The compound of formula (I), is commercially known as Saroglitazar. This compound (Saroglitazar) is dosed to patients in need thereof as its Magnesium salt (Ia) for the treatment of one or more of the diseases described above.

The compound of formula (1a) was prepared as per the processes disclosed in the prior art such as those mentioned elsewhere in the specification. The efficacy of the compound in the treatment of PBC may be evaluated in vivo as described in the Examples

EXAMPLES

The invention now being generally described, will be more readily understood by reference to the following examples, which are included merely for purposes of illustration of certain aspects and embodiments of the present invention, and are not intended to limit the invention.

Example 1: Efficacy of Compound of Formula (Ia) in Carbon Tetrachloride-Induced Liver Fibrosis in Male Sprague Dawley Rats Purpose The objective of this study was to evaluate the efficacy of Compound of formula (Ia) in hepatic fibrosis induced by carbon tetrachloride administration in male Sprague Dawley rats.

Methods

To assess the effect of Compound of formula (Ia) on the progression of established hepatic fibrosis, fibrosis was induced in rats by twice weekly carbon tetrachloride ($CCl_4$) injections for 2 weeks via an intraperitoneal route. Compound (Ia) (0.4 and 4 mg/kg/day), pioglitazone (10 mg/kg/day), fenofibrate (100 mg/kg/day) or vehicle (Tween 80 and 0.5% sodium salt of carboxymethylcellulose at ratio of 0.5:99.5) was then orally administered for 4 weeks to animals concomitantly with continued $CCl_4$ injections.

After 4 weeks of treatment, blood samples were collected 1 h post-dose, for estimation of non-fasted serum ALT and other serum parameters. All the animals were sacrificed; liver was quickly removed, weighed and fixed in 10% formalin for histological analysis or snap frozen in liquid nitrogen for other assays. Light microscopic examination of liver tissue was performed using standard hematoxylin and eosin (H&E) staining. Hepatic fibrosis was accessed by Masson's trichrome staining method.

Results

When administered intraperitoneally to Sprague Dawley rats for a period of 6 weeks, $CCl_4$ produced hepatic fibrosis. Compound of formula (Ia) protected the animals from further deterioration and exhibited a dose-dependent reversal of $CCl_4$-induced liver fibrosis. The microscopic quantification of fibrosis demonstrated that Compound (Ia) stopped the progression of established liver fibrosis and accelerated liver recovery, as indicated histological improvements observed in FIG. 1, hematoxylin and eosin H&E and Masson's trichrome staining of liver tissues.

Conclusions

Carbon tetrachloride when administered intraperitoneally to SD rats for a period of 6 weeks produced hepatic fibrosis. Compound of formula (Ia) protected the animals from further deterioration and showed dose dependent reversal of $CCl_4$-induced liver fibrosis.

Example 2: Antifibrotic Activity of Compound of Formula (Ia) Will be Evaluated in the Thioacetamide (TAA) Model of Liver Fibrosis in Rats Purpose The objective of this study is to evaluate the efficacy of Compound (Ia) in hepatic fibrosis and induced by thioacetamide (TAA) administration in male Sprague Dawley rats. Secondarily hepatic fibrosis causes increased portal pressure so effect on portal pressure will also be evaluated in this model.

Methods

To assess the effect of Compound (Ia) on the progression of established hepatic fibrosis, fibrosis will be induced in rats by intraperitoneal TAA injections (50-150 mg/kg) or, and animals will be treated with Compound (Ia) at 4 mg/kg dose or vehicle according to the following study design. First TAA and or test compound will be given simultaneously for a period of 6 weeks and in second design first TAA was administered and for a period of 6 weeks and then week-6 onwards treatment will be initiated at 4 mg/kg dose of Compound (Ia).

After 6 weeks of treatment, blood samples will be collected 1 h post-dose, for estimation of non-fasted serum ALT and other serum parameters and animals will be subjected for in-vivo hemodynamic parameter measurement to measure portal pressure. All the animals will be sacrificed; liver will be quickly removed, weighed and fixed in 10% formalin for histological analysis or snap frozen in liquid nitrogen for other assays. Light microscopic examination of liver tissue was performed using standard hematoxylin and eosin (H&E) staining. Hepatic fibrosis was accessed by Masson's trichrome staining method.

Results

Disease Control animals administered with TAA and vehicle may show fibrosis and might be cirrhotic while animals administered TAA plus Compound (Ia) may show mild fibrosis and may have statistically significant decreases in portal pressure, compared to respective control groups.

The microscopic quantification of fibrosis may show that Compound (Ia) has stopped the progression of established liver fibrosis and accelerated liver recovery, as indicated histological improvements observed following H&E and Masson's trichrome staining of liver tissues.

Example 3: A Phase 2, Prospective, Multicenter, Randomized, Open Label, Study to Evaluate Safety, Tolerability and Efficacy of Saroglitazar (as its Magnesium Salt) in Patients with Primary Biliary Cholangitis Objectives:

The purpose of this study is to evaluate the safety tolerability, and efficacy of Saroglitazar (as its Magnesium salt) in patients with Primary Biliary Cholangitis.

Primary Evaluation Criteria:

To investigate the effect of a 16-week treatment regimen of Saroglitazar (as its Magnesium salt), 4 mg on alkaline phosphatase (ALP) levels in patients with Primary Biliary Cholangitis Secondary Endpoints To compare the effect of Saroglitazar (as its Magnesium salt) compared to Obeticholic Acid for the following parameters following a 16-week treatment regimen:
    Alkaline Phosphatase
    Pruritus
    Lipids profile: TG, TC, HDL, LDL, and VLDL
    Liver function test: GGT, ALT, AST, bilirubin and albumin
    Quality of life
    Safety and tolerability of Saroglitazar Magnesium Safety
    Frequency and severity of adverse events and serious adverse events
    Clinical laboratory testing (hematology, clinical chemistry and urinalysis)
    Twelve-lead electrocardiogram (ECG)
    Vital signs Inclusion Criteria:
    Males or females, between 18 and 75 years of age, inclusive
    Stable dose of ursodeoxycholic acid (UDCA) for >3 months prior to screening American Association for the Study of Liver Disease [AASLD] and European Association for study of the Liver [EASL] Practice Guidelines; [Lindor 2009; EASL 2009]), as demonstrated by the presence of ≥2 of the following 3 diagnostic factors:
  History of elevated Alkaline Phosphatase levels for at least 6 months prior to Day 0
  Positive antimitochondrial antibodies (AMA) titer or if AMA negative or in low titer (<1:80) PBC specific antibodies (anti-GP210 and/or anti-SP100 and/or antibodies against the major M2 components (PDC-E2, 2-oxo-glutaric acid dehydrogenase complex)
  Liver biopsy consistent with PBC.
ALP ≥1.67× upper limit of normal (ULN)
Subjects must have a body mass index (BMI) within the range of 18-35 kg/m².
Contraception: Female patients must be postmenopausal, surgically sterile, or if premenopausal, be prepared to use ≥1 effective method of contraception during the trial. Effective methods of contraception are considered to be Hormonal (e.g., contraceptive pill, patch, intramuscular implant or injection); or Double barrier method, i.e., (a) condom (male or female) or (b) diaphragm, with spermicide; or Intrauterine device (IUD); or Vasectomy (partner).
Must provide written informed consent and agree to comply with the trial protocol.

Exclusion Criteria:
  Consumption of >3 units of alcohol per day (>21 units per week) if male and >2 units of alcohol per day (>14 units per week) if female for at least 3 consecutive months in the last 5 years (Note: 1 unit=12 ounces of beer, 4 ounces of wine or 1 ounce of spirits/hard liquor).
  History or presence of other concomitant liver diseases including:
    Hepatitis B or C virus (HCV, HBV) infection
    Primary sclerosing cholangitis (PSC)
    Alcoholic liver disease
    Definite autoimmune liver disease or overlap hepatitis
    Non-alcoholic steatohepatitis (NASH)
  Cirrhosis with complications, including history or presence of: spontaneous bacterial peritonitis, hepatocellular carcinoma, bilirubin >2×ULN, ascites, encephalopathy
  History of any venous thromboembolism, TIA, intracranial hemorrhage, neoplasm, arteriovenous malformation, vasculitis, bleeding disorder, coagulation disorders or screening blood tests that indicate altered coagulability (e.g. platelet count, aPTT, PTT or TT tests).
  Unstable cardiovascular disease, including:
    Unstable angina, (i.e., new or worsening symptoms of coronary heart disease within the past 3 months), acute coronary syndrome within the past 6 months, acute myocardial infarction in the past 3 months or heart failure of New York Heart Association class (III-IV) or worsening congestive heart failure, or coronary artery intervention, within the past 6 months
    history of (within prior 3 months) or current unstable cardiac dysrhythmias
    uncontrolled hypertension (systolic blood pressure [BP]>160 mmHg and/or diastolic BP >100 mmHg)
    stroke or transient ischemic attack within the prior 6 months
  History of malignancy in the past 5 years and/or active neoplasm with the exception of resolved superficial non-melanoma skin cancer.
  Contraindications to saroglitazar magnesium or has any conditions affecting the ability to evaluate the effects of Saroglitazar magnesium.
  Use of thiazolidinedione (pioglitazone, rosiglitazone).
  Known allergy, sensitivity or intolerance to the study drug, active comparator or formulation ingredients.
  Participation in any other therapeutic clinical study in the past 3 months, including participation in any other PBC clinical trials.
  Illicit substance abuse within the past 12 months.
  History or other evidence of severe illness or any other conditions that would make the patient, in the opinion of the investigator, unsuitable for the study (such as poorly controlled psychiatric disease, HIV, coronary artery disease or active gastrointestinal conditions that might interfere with drug absorption).

Example 4: A Phase 2, Prospective, Multicenter, Randomized, Open Label, Study to Evaluate Safety, Tolerability and Efficacy of Saroglitazar Magnesium in Human Patients with Primary Biliary Cholangitis Human patients suffering from primary biliary cholangitis are to be administered saroglitazar magnesium salt once per day in the morning before receiving any food in patients. The saroglitazar magnesium salt is to be administered orally at a dose of 2 mg or 4 mg. The saroglitazar magnesium salt is to be administered daily for a duration of 16 weeks. Alkaline phosphatase (ALP) levels in patients will be monitored. In addition, the following secondary end-points will be monitored:
  Alkaline Phosphatase
  Pruritus
  Lipids profile: TG, TC, HDL, LDL, and VLDL
  Liver function test: GGT, ALT, AST, bilirubin and albumin
  Quality of life
  Safety and tolerability of Saroglitazar Magnesium Patient selection criteria include:
(1) Inclusion Criteria:
  Males or females, between 18 and 75 years of age, inclusive
  Patients on therapeutic doses of Ursodeoxycholic acid (UDCA) for ≥12 months and stable therapy for ≥3 months prior to enrolment
  History of confirmed Primary Biliary Cholangitis Diagnosis, based on American Association for the Study of Liver Disease [AASLD] and European Association for Study of the Liver [EASL] Practice Guidelines; [Lindor 2009; EASL 2009], as demonstrated by the presence of at least 2 of the following 3 diagnostic factors:
    History of elevated Alkaline Phosphatase levels for at least 6 months prior to Screening Visit 1
    Positive antimitochondrial antibodies (AMA) titer or if AMA negative or in low titer (<1:80) PBC specific antibodies (anti-GP210 and/or anti-SP100 and/or antibodies against the major M2 components (PDC-E2, 2-oxo-glutaric acid dehydrogenase complex)
    Liver biopsy consistent with PBC.
  ALP ≥1.67× upper limit of normal (ULN) at Visit 1 and Visit 2 and with <30% variance between the levels from Visit 1 to Visit 2.
  Subjects must have a body mass index (BMI) within the range of 18-35 kg/m².
  Contraception: Female patients must be postmenopausal, surgically sterile, or if premenopausal, be prepared to use ≥1 effective method of contraception during the trial. Effective methods of contraception are considered to be Hormonal (e.g., contraceptive pill, patch, intramuscular implant or injection); or Double barrier method, i.e., (a) condom (male or female) or (b) diaphragm, with spermicide; or Intrauterine device (IUD); or Vasectomy (partner).

Must provide written informed consent and agree to comply with the trial protocol.

(2) Exclusion Criteria:

Consumption of >3 units of alcohol per day (>21 units per week) if male and >2 units of alcohol per day (>14 units per week) if female for at least 3 consecutive months in the last 5 years (Note: 1 unit=12 ounces of beer, 4 ounces of wine or 1 ounce of spirits/hard liquor).

History or presence of other concomitant liver diseases including:
Hepatitis B or C virus (HCV, HBV) infection
Primary sclerosing cholangitis (PSC)
Alcoholic liver disease
Definite autoimmune liver disease or overlap hepatitis
Non-alcoholic steatohepatitis (NASH)

Cirrhosis with complications, including history or presence of: spontaneous bacterial peritonitis, hepatocellular carcinoma, bilirubin >2×ULN, ascites, encephalopathy, known esophageal varices or history of variceal bleeding and active or history of hepatorenal syndrome History of any venous thromboembolism, TIA, intracranial hemorrhage, neoplasm, arteriovenous malformation, vasculitis, bleeding disorder, coagulation disorders or screening blood tests that indicate altered coagulability (e.g. platelet count, aPTT, PTT or TT tests).

Patients with baseline abnormal total bilirubin and INR.
Patient with Gilbert's disease.

Patients with >30% variance in the levels of AST, ALT, total bilirubin (TB) and INR from Visit 1 to Visit 2.

Patients with mild, moderate and severe renal impairment i.e. estimated glomerular filtration rate (eGFR)<90 mL/min/1.73 m² at Visit 1 (calculated using Chronic Kidney Disease Epidemiology Collaboration (CKD-EPI) equation).

Abnormal total creatine kinase (CK), lipase and amylase at Visit 1.

Unstable cardiovascular disease, including:
Unstable angina, (i.e., new or worsening symptoms of coronary heart disease within the past 3 months), acute coronary syndrome within the past 6 months, acute myocardial infarction in the past 3 months or heart failure of New York Heart Association class (III-IV) or worsening congestive heart failure, or coronary artery intervention, within the past 6 months
history of (within prior 3 months) or current unstable cardiac dysrhythmias
uncontrolled hypertension (systolic blood pressure [BP]>160 mmHg and/or diastolic BP >100 mmHg)
stroke or transient ischemic attack within the prior 6 months History of malignancy in the past 5 years and/or active neoplasm with the exception of resolved superficial non-melanoma skin cancer.

Contraindications to saroglitazar magnesium or has any conditions affecting the ability to evaluate the effects of Saroglitazar magnesium.

Patients who are on cerivastatin treatment at the time of enrolment

Known allergy, sensitivity or intolerance to the study drug, active comparator or formulation ingredients.

Participation in any other therapeutic clinical study in the past 3 months.

Illicit substance abuse within the past 6 months.

History or other evidence of severe illness or any other conditions that would make the patient,
in the opinion of the investigator, unsuitable for the study (such as poorly controlled psychiatric disease, human immunodeficiency virus (HIV), coronary artery disease or active gastrointestinal conditions that might interfere with drug absorption)

The study will analyze three groups of patients. The first group of patients is to receive saroglitazar magnesium salt is once per day orally at a dose of 2 mg. The second group of patients is to receive saroglitazar magnesium salt is once per day orally at a dose of 4 mg. The third group of patients is to receive placebo.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. A method of treating primary biliary cholangitis, comprising administering orally and once daily to a human in need thereof a therapeutically effective amount of saroglitazar magnesium salt, to treat the primary biliary cholangitis; wherein saroglitazar is represented by:

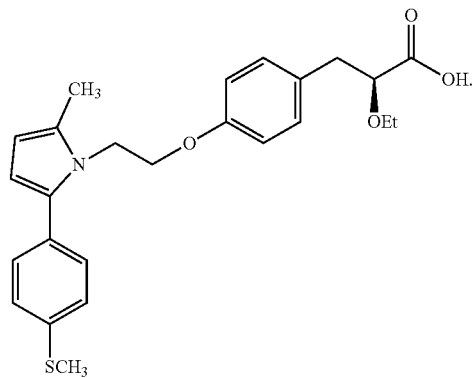

2. The method of claim 1, wherein about 4 mg saroglitazar magnesium salt is administered.

3. The method of claim 1, wherein about 2 mg saroglitazar magnesium salt is administered.

4. The method of claim 1, wherein saroglitazar magnesium salt is the sole therapeutic agent for treating the primary biliary cholangitis.

5. The method of claim 1, wherein administering occurs for at least 16 weeks.

6. A method of treating primary biliary cholangitis, comprising administering orally and once daily to a human in need thereof a pharmaceutical formulation in the form of a tablet or a capsule, the pharmaceutical formulation comprising a therapeutically effective amount of saroglitazar magnesium salt; and a pharmaceutical excipient, to treat the primary biliary cholangitis; wherein saroglitazar is represented by:

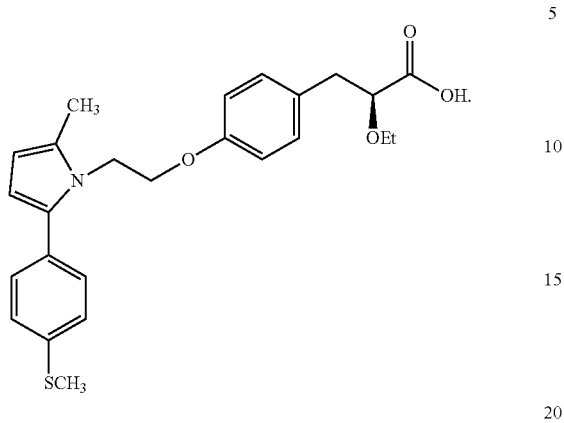

7. The method of claim 6, wherein saroglitazar magnesium salt is the sole therapeutic agent in the pharmaceutical formulation.

8. The method of claim 6, wherein saroglitazar magnesium salt is the sole therapeutic agent for treating the primary biliary cholangitis.

9. The method of claim 6, wherein the pharmaceutical formulation comprises about 2 mg saroglitazar magnesium salt.

10. The method of claim 6, wherein the pharmaceutical formulation comprises about 4 mg saroglitazar magnesium salt.

* * * * *